(12) United States Patent
Schneider

(10) Patent No.: US 11,266,544 B2
(45) Date of Patent: Mar. 8, 2022

(54) METHOD AND APPARATUS FOR MAKING PATTERNED APERTURED SUBSTRATES

(71) Applicant: The Procter & Gamble Company, Cincinnati, OH (US)

(72) Inventor: Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 384 days.

(21) Appl. No.: 16/571,495

(22) Filed: Sep. 16, 2019

(65) Prior Publication Data
US 2020/0085637 A1 Mar. 19, 2020

Related U.S. Application Data

(60) Provisional application No. 62/733,107, filed on Sep. 19, 2018.

(51) Int. Cl.
| | |
|---|---|
| *A61F 13/15* | (2006.01) |
| *B30B 3/00* | (2006.01) |
| *B29C 63/42* | (2006.01) |
| *B29C 65/70* | (2006.01) |
| *A61F 13/84* | (2006.01) |
| *B29L 31/48* | (2006.01) |

(52) U.S. Cl.
CPC .. *A61F 13/15731* (2013.01); *A61F 13/15764* (2013.01); *B29C 63/42* (2013.01); *B29C 65/70* (2013.01); *B30B 3/005* (2013.01); *A61F 2013/8497* (2013.01); *B29L 2031/4878* (2013.01)

(58) Field of Classification Search
None
See application file for complete search history.

(56) References Cited

U.S. PATENT DOCUMENTS

| | | |
|---|---|---|
| 2,075,189 A | 3/1937 | Galligan |
| 3,025,199 A | 3/1962 | Harwood |
| 3,113,225 A | 12/1963 | Claus |
| 3,562,041 A | 2/1971 | Robertson |
| 3,733,238 A | 5/1973 | Long |

(Continued)

OTHER PUBLICATIONS

EP Search Report, dated Feb. 10, 2020, 5 pages.

*Primary Examiner* — Barbara J Musser
(74) *Attorney, Agent, or Firm* — Jay A. Krebs; Charles R. Matson

(57) ABSTRACT

The present disclosure relates to apparatuses and methods for making patterned apertured substrates that may be used as components of absorbent articles. During the manufacturing processes, a precursor substrate advances in a machine direction between a pattern roll and an anvil roll. The pattern roll rotates about an axis of rotation and includes a plurality of pattern surfaces, wherein the substrate is compressed between the anvil roll and the pattern surfaces of the pattern roll to form discrete bond regions in the substrate. The pattern surfaces on the pattern roll are formed on continuous threads extending circumferentially around the axis of rotation along helical paths parallel with each other. As such, the pattern surfaces press the substrate against the outer circumferential surface of the anvil roll in the different axial locations along the cross direction as the pattern roll rotates when forming the discrete bond regions.

20 Claims, 19 Drawing Sheets

(56) References Cited

U.S. PATENT DOCUMENTS

| | | |
|---|---|---|
| 3,848,594 A | 11/1974 | Buell |
| 3,860,003 A | 1/1975 | Buell |
| 4,107,364 A | 8/1978 | Sisson |
| 4,209,563 A | 6/1980 | Sisson |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit et al. |
| 4,556,146 A | 12/1985 | Swanson et al. |
| 4,589,876 A | 5/1986 | Van Tilburg |
| 4,610,678 A | 9/1986 | Weisman et al. |
| 4,662,875 A | 5/1987 | Hirotsu |
| 4,673,402 A | 6/1987 | Weisman |
| 4,687,478 A | 8/1987 | Van Tilburg |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany |
| 4,834,741 A | 5/1989 | Sabee |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz |
| 4,940,464 A | 7/1990 | Van Gompel et al. |
| 4,946,527 A | 8/1990 | Battrell |
| 4,950,264 A | 8/1990 | Osborn, III |
| 5,009,653 A | 4/1991 | Osborn, III |
| 5,092,861 A | 3/1992 | Nomura |
| 5,110,403 A | 5/1992 | Ehlert |
| 5,151,092 A | 9/1992 | Buell |
| 5,167,897 A | 12/1992 | Weber et al. |
| 5,221,274 A | 6/1993 | Buell |
| 5,246,433 A | 9/1993 | Hasse |
| 5,267,992 A | 12/1993 | Van Tilburg |
| 5,330,458 A | 7/1994 | Buell |
| 5,342,277 A * | 8/1994 | Steiner .................. B30B 3/005 492/26 |
| 5,360,420 A | 11/1994 | Cook et al. |
| 5,562,646 A | 10/1996 | Goldman et al. |
| 5,569,234 A | 10/1996 | Buell |
| 5,599,335 A | 2/1997 | Goldman et al. |
| 5,628,097 A | 5/1997 | Benson et al. |
| 5,643,588 A | 7/1997 | Roe et al. |
| 5,669,894 A | 9/1997 | Goldman et al. |
| 5,674,216 A | 10/1997 | Buell et al. |
| 5,702,551 A | 12/1997 | Huber et al. |
| 5,735,840 A | 4/1998 | Kline et al. |
| 5,897,545 A | 4/1999 | Kline et al. |
| 5,916,661 A | 6/1999 | Benson et al. |
| 5,928,212 A | 7/1999 | Kline et al. |
| 5,957,908 A | 9/1999 | Kline et al. |
| 5,968,025 A | 10/1999 | Roe et al. |
| 6,004,893 A | 12/1999 | Van Tilburg |
| 6,036,796 A | 3/2000 | Halbert et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,153,209 A | 11/2000 | Vega et al. |
| 6,251,097 B1 | 6/2001 | Kline et al. |
| 6,410,129 B2 | 6/2002 | Zhang et al. |
| 6,426,444 B2 | 7/2002 | Roe et al. |
| 6,432,098 B1 | 8/2002 | Kline et al. |
| 6,508,641 B1 | 1/2003 | Kubik |
| 6,545,197 B1 | 4/2003 | Mueller et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,645,330 B2 | 11/2003 | Pargass et al. |
| 6,669,618 B2 | 12/2003 | Reising et al. |
| 6,790,798 B1 | 9/2004 | Suzuki et al. |
| 6,825,393 B2 | 11/2004 | Roe et al. |
| 6,861,571 B1 | 3/2005 | Roe et al. |
| 7,371,302 B2 | 5/2008 | Miyamoto et al. |
| 7,569,039 B2 | 8/2009 | Matsuda et al. |
| 8,226,625 B2 | 7/2012 | Turner et al. |
| 8,226,626 B2 | 7/2012 | Turner et al. |
| 8,231,595 B2 | 7/2012 | Turner et al. |
| 8,388,594 B2 | 3/2013 | Turner et al. |
| 2003/0021951 A1 | 1/2003 | Desai |
| 2003/0233082 A1 | 12/2003 | Kline |
| 2004/0097895 A1 | 5/2004 | Busam et al. |
| 2004/0158212 A1 | 8/2004 | Ponomarenko et al. |
| 2005/0107764 A1 | 5/2005 | Matsuda et al. |
| 2007/0078427 A1 | 4/2007 | Raycheck |
| 2007/0093769 A1 | 4/2007 | Kline |
| 2009/0104831 A1 | 4/2009 | Bornemann |
| 2009/0312730 A1 | 12/2009 | LaVon et al. |
| 2012/0061015 A1 | 3/2012 | LaVon et al. |
| 2012/0061016 A1 | 3/2012 | LaVon et al. |
| 2013/0072887 A1 | 3/2013 | Lavon et al. |
| 2013/0211356 A1 | 8/2013 | Nishikawa et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0306226 A1 | 11/2013 | Zink et al. |
| 2015/0174857 A1 | 6/2015 | Schmitz |
| 2016/0136014 A1 | 5/2016 | Arora et al. |
| 2016/0235590 A1 | 8/2016 | Coe et al. |

* cited by examiner

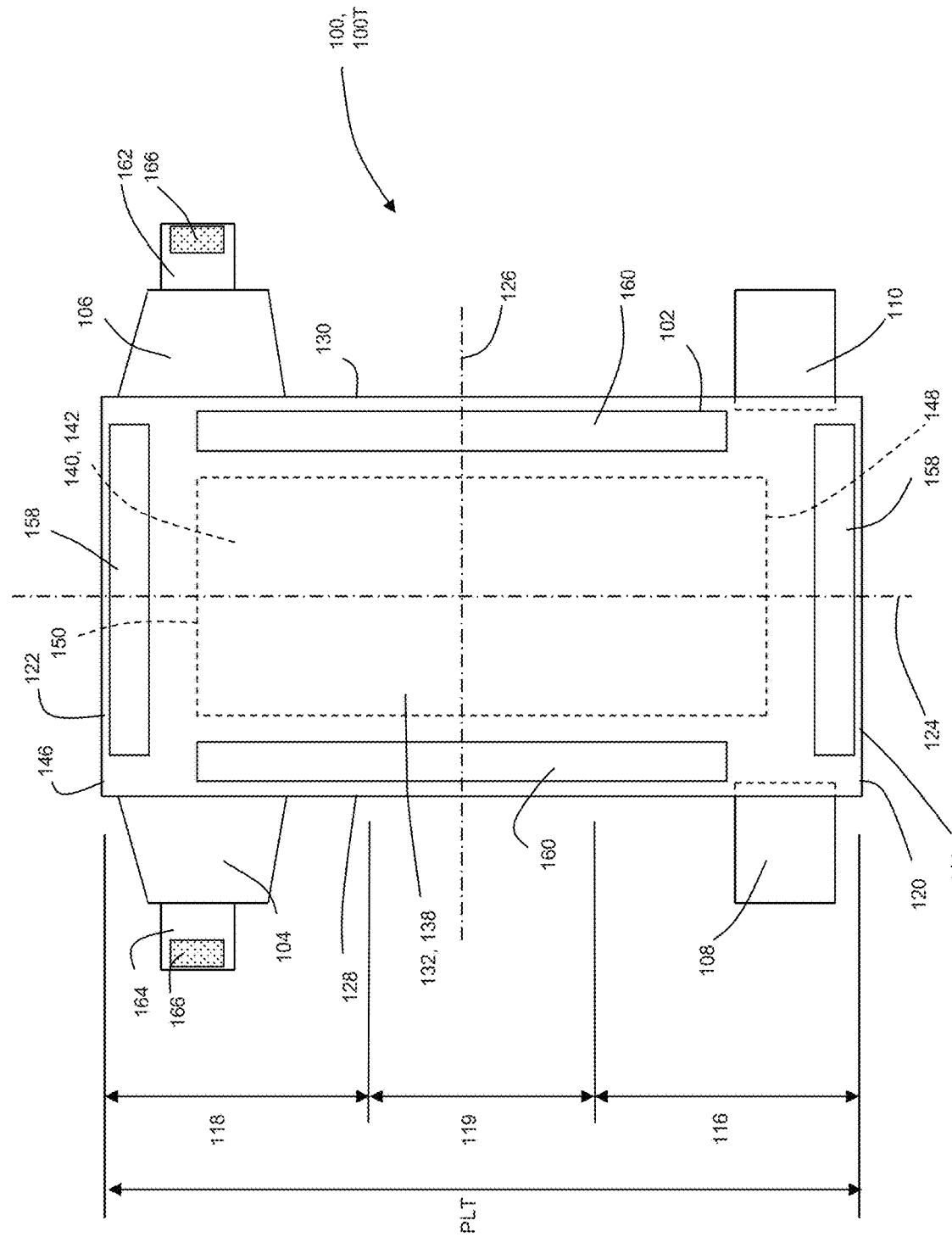

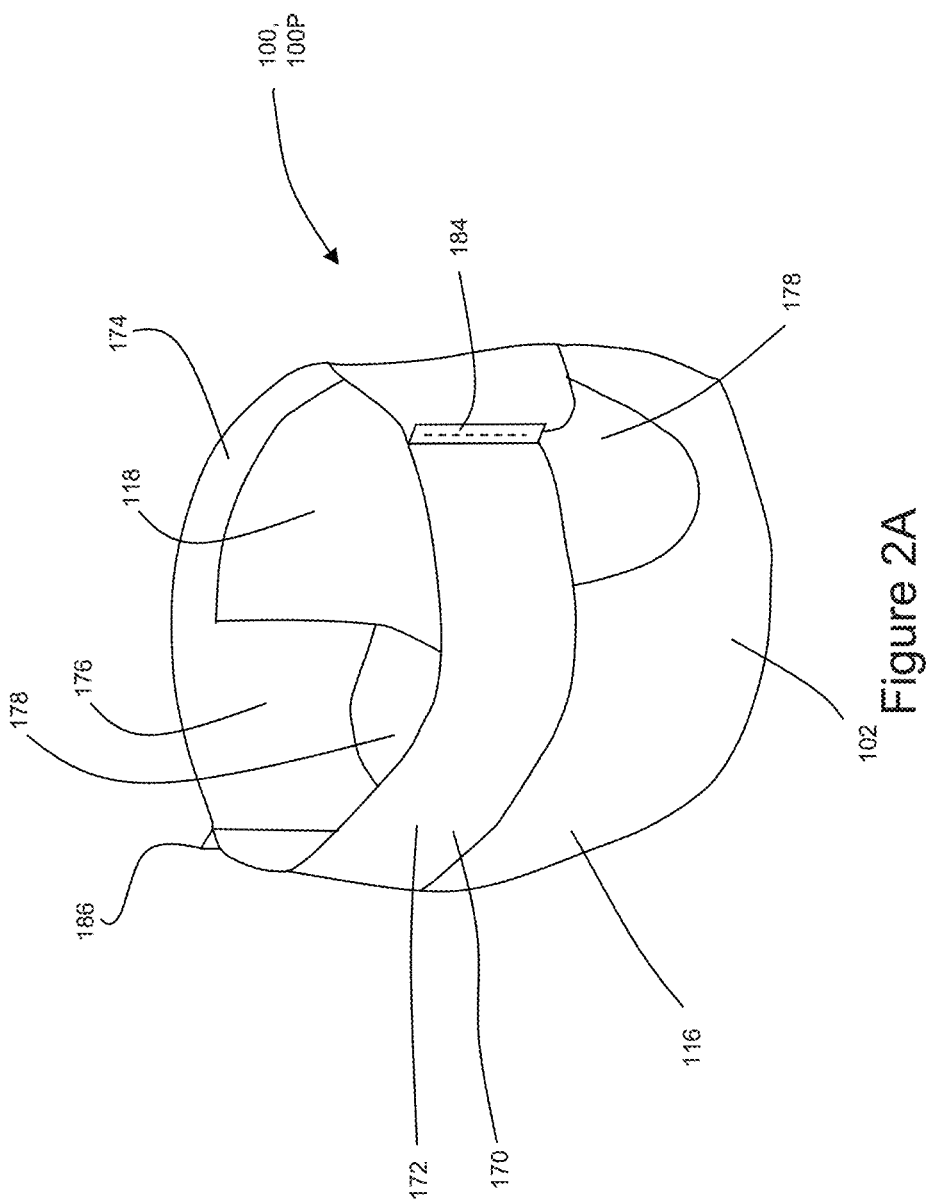

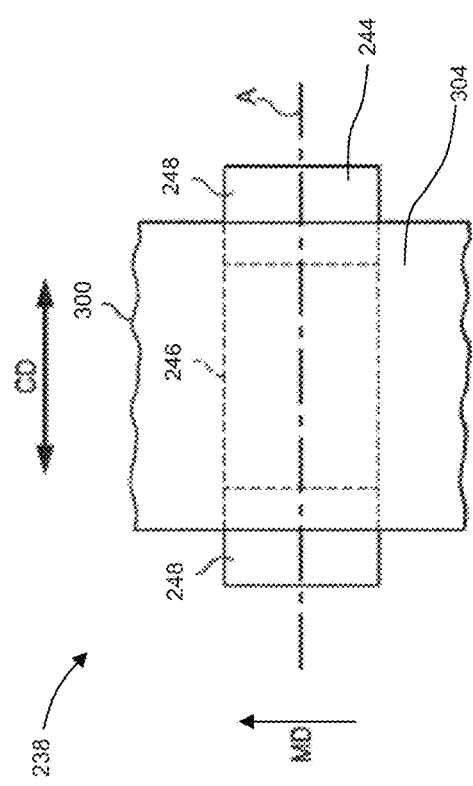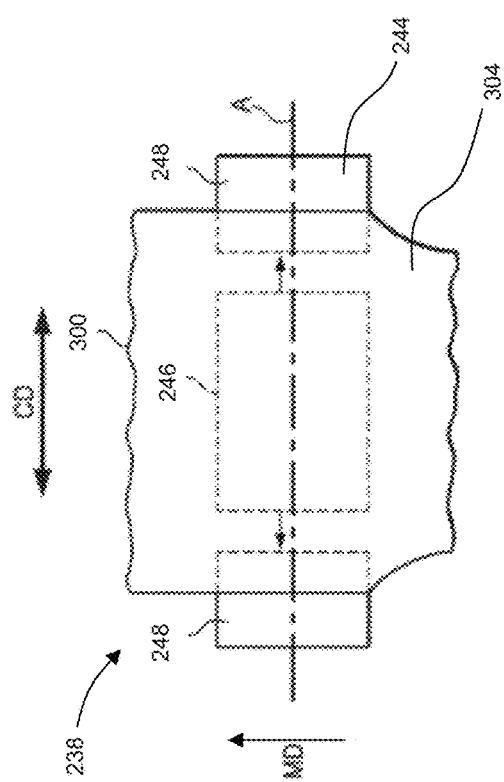

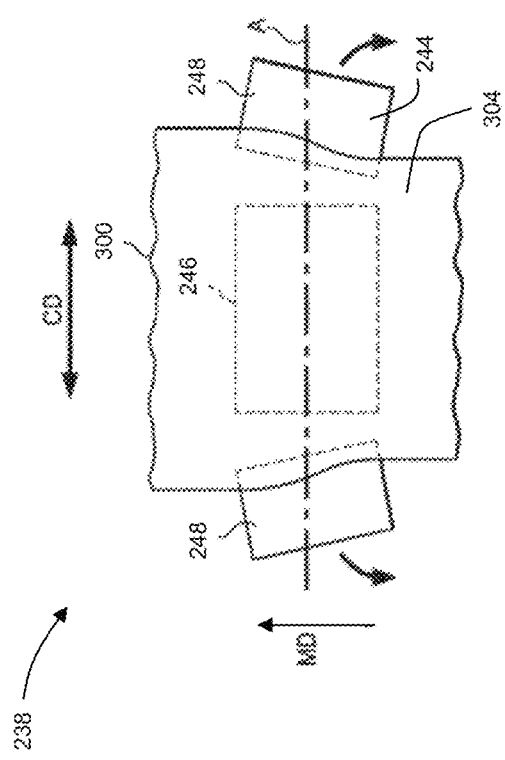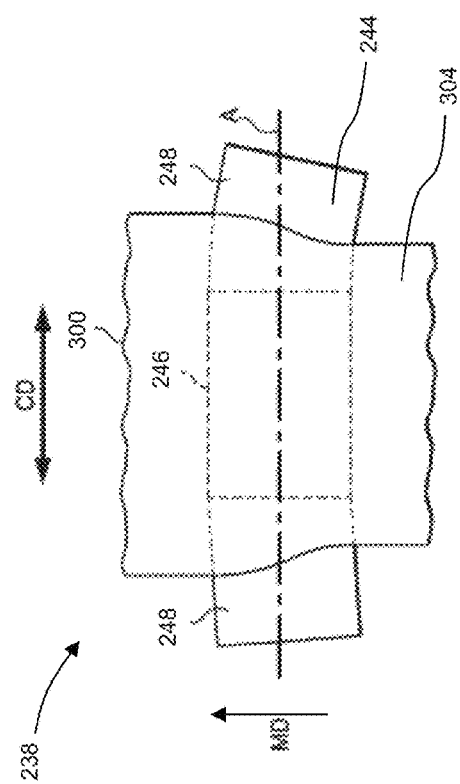

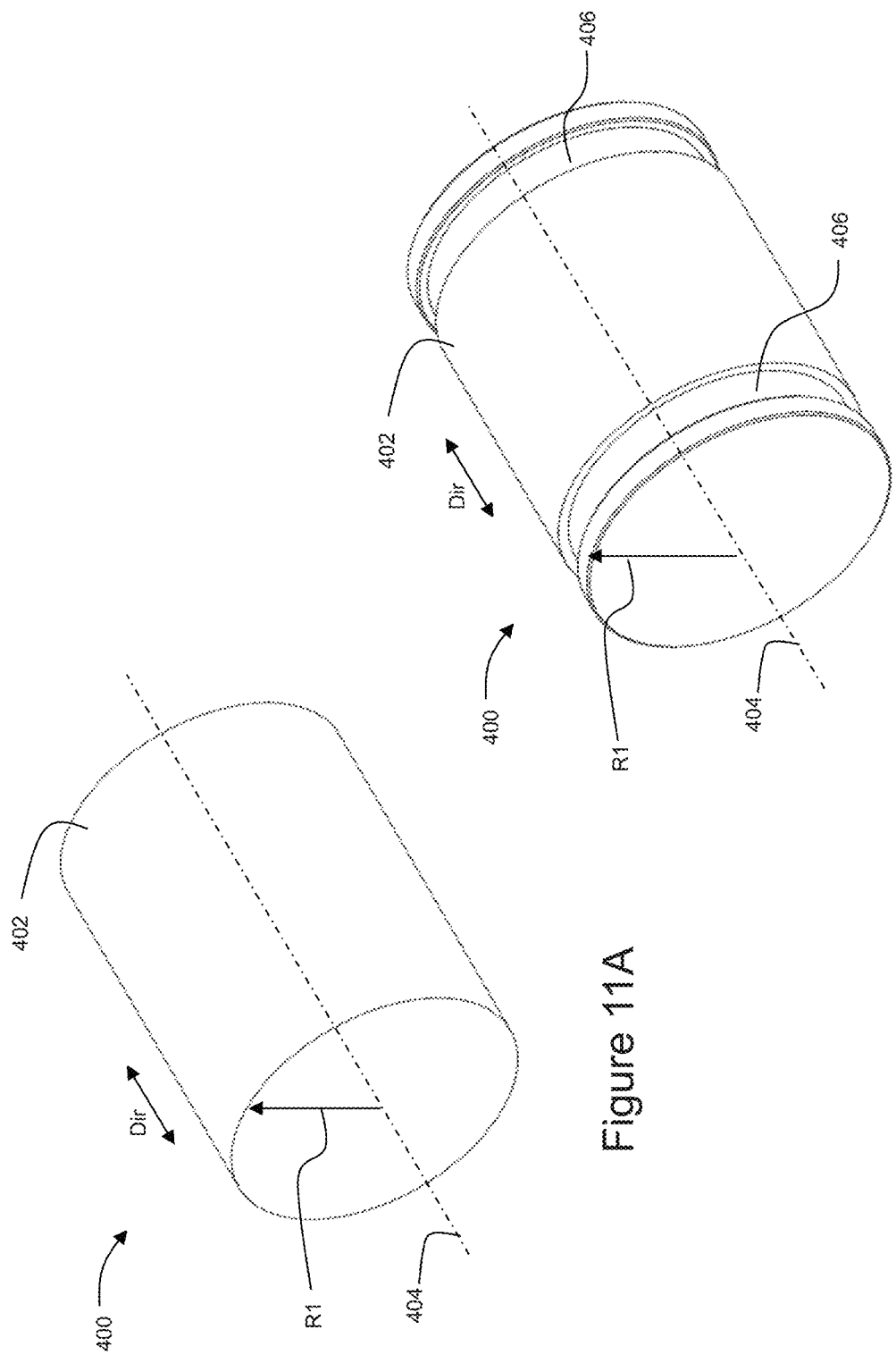

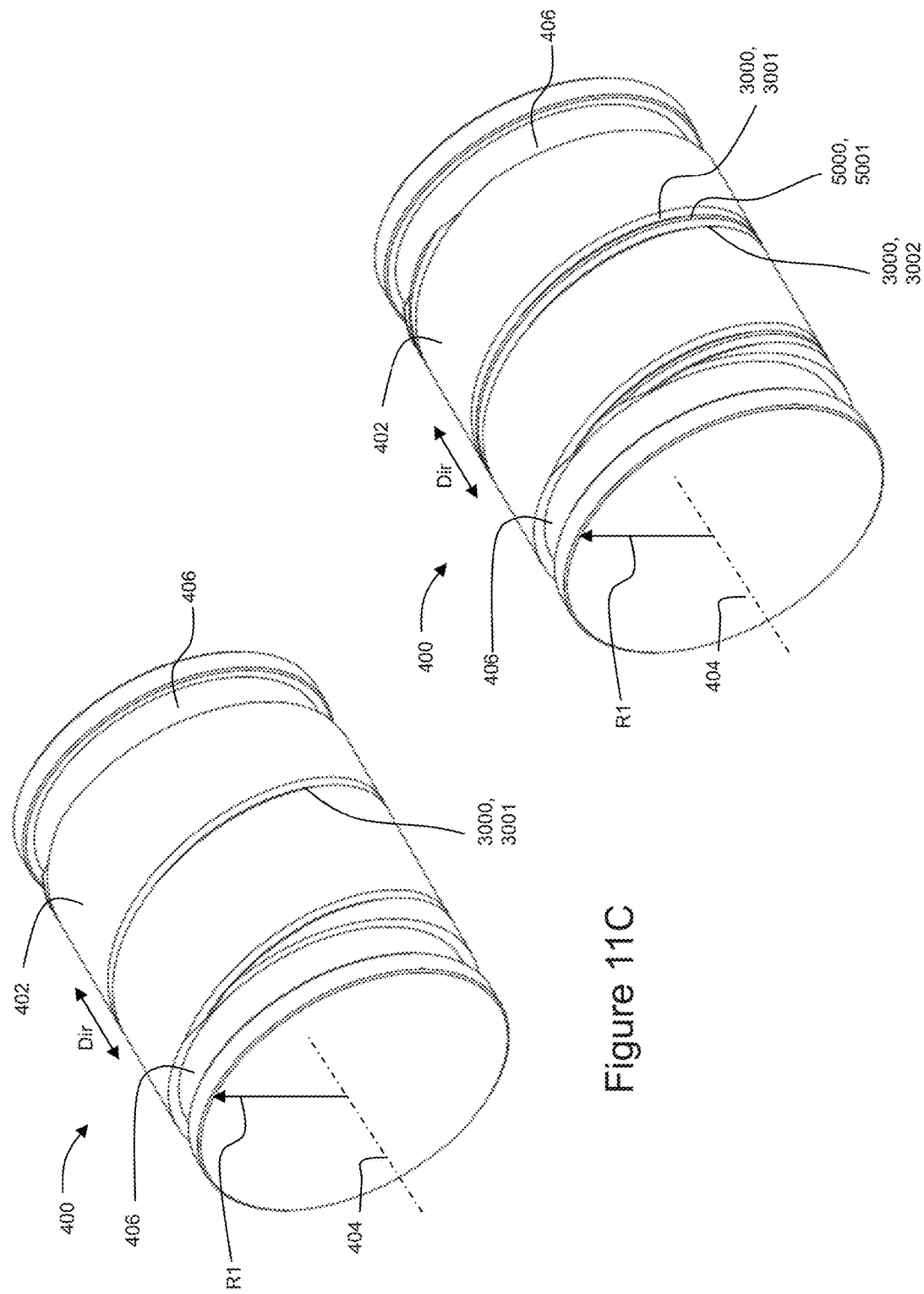

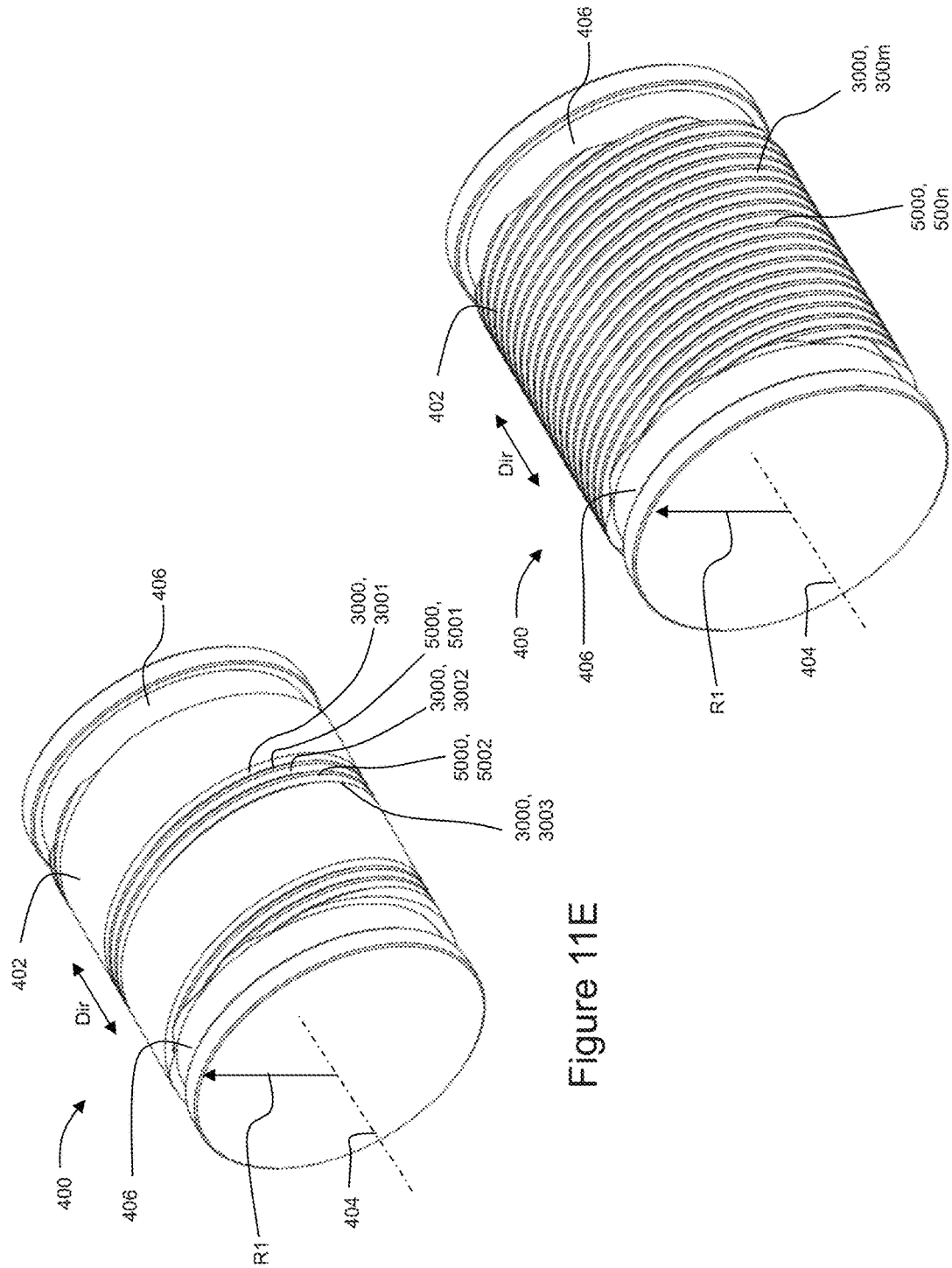

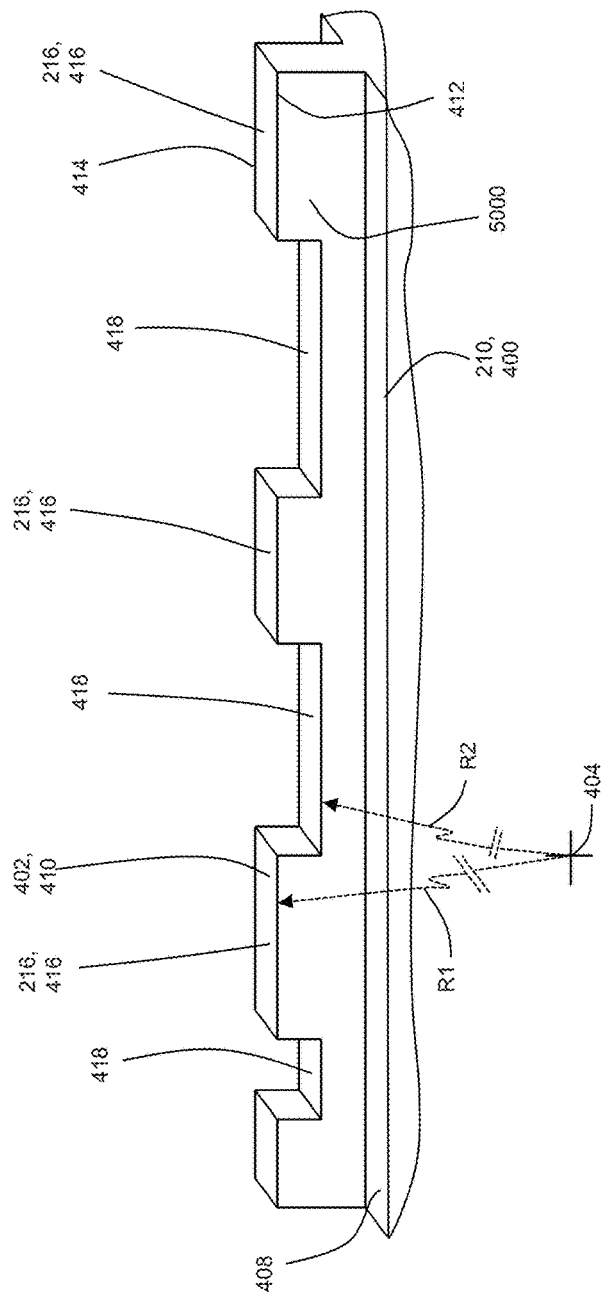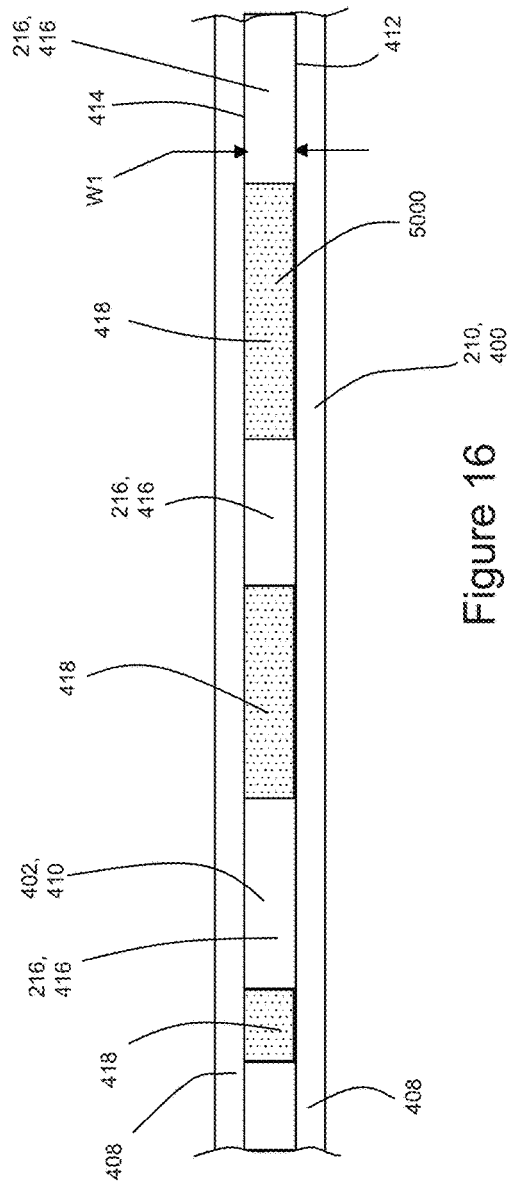

US 11,266,544 B2

METHOD AND APPARATUS FOR MAKING PATTERNED APERTURED SUBSTRATES

CROSS REFERENCE TO RELATED APPLICATIONS

This application claims the benefit of U.S. Provisional Application No. 62/733,107, filed on Sep. 19, 2018, the entirety of which is incorporated by reference herein.

FIELD OF THE INVENTION

The present disclosure relates to methods for manufacturing absorbent articles, and more particularly, to apparatuses and methods for making patterned apertured substrates that may be used as components of absorbent articles.

BACKGROUND OF THE INVENTION

Along an assembly line, various types of disposable absorbent articles, such as diapers, sanitary napkins, and pant liners, may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Webs of material and component parts used to manufacture sanitary napkins and/or panty liners may include: backsheets, topsheets, secondary topsheets, absorbent core components, release paper wrappers, and the like. Once the desired component parts are assembled, the advancing web(s) and component parts are subjected to a final knife cut to separate the web(s) into discrete absorbent articles. The absorbent articles may also sometimes be folded and/or individually wrapped.

Some components of absorbent articles may include apertured webs. Various methods and apparatuses may be used for forming apertures in an advancing web and/or otherwise modify an advancing web during the manufacturing process. For example, in some operations, a web may advance in a machine direction between a pattern roll and a smooth anvil roller to create a plurality of weakened, melt stabilized locations in the web. The weakened, melt stabilized locations in the web may correspond with an arrangement of pattern surfaces on the pattern roll. The web may then be stretched in a cross direction to rupture the plurality of weakened, melt stabilized locations in the web, thereby creating a plurality of apertures in the web coincident with the plurality of weakened, melt stabilized locations.

In such operations, repetitive contact between the pattern surfaces on the pattern roll and the anvil roll may cause excessive wear on the anvil roll. In some configurations, the pattern roll and the anvil roll may be sized such that the pattern surfaces contact the anvil roll in the same circumferential and axial locations during use. Thus, the anvil roll may exhibit localized wear in these locations, necessitating relative frequent repair or replacement of the anvil roll.

Consequently, it would be beneficial to provide methods and apparatuses with pattern rolls that are configured to operate to help mitigate localized wear on anvil rolls and wherein such pattern rolls may be designed for ease of manufacture at relatively low costs.

SUMMARY OF THE INVENTION

In one form, a method for making an apertured substrate comprises: rotating a pattern roll about an axis of rotation extending in a cross direction, the pattern roll comprising an outer circumferential surface, the pattern roll comprising: a number, n, of continuous threads extending circumferentially around the axis of rotation along a helical path parallel with each other, wherein n is 2 or greater; wherein each thread protrudes radially outward from the outer circumferential surface; wherein each thread comprises first outer surfaces and second outer surfaces intermittently arranged circumferentially around the axis of rotation along a length of each thread; wherein the first outer surfaces are positioned radially outward from the axis of rotation by a first radius R1; wherein the second outer surfaces are positioned radially outward from the axis of rotation by a second radius R2 less than the first radius R1; wherein each first outer surface extends axially in the cross direction, from a first edge to a second edge; wherein the first edges of neighboring threads are separated by a pitch length, PL, extending in the cross direction; wherein the first edges of a first thread are separated from first edges of the first thread by a lead length, LL, extending in the cross direction, wherein [LL=PL*n]; and wherein each thread comprises a helix angle, wherein

[helix angle=arctan((2*Π*R1)/(LL)), wherein 45°<helix angle<90°];

rotating an anvil roll adjacent the pattern roll; advancing a substrate in a machine direction between the pattern roll and the anvil roll, the machine direction being substantially perpendicular to the cross direction; compressing the substrate between the anvil roll and the first surfaces of the threads to form discrete bond regions in the substrate; and stretching the substrate in the cross direction to cause the discrete bond regions to rupture and form apertures.

In another form, an apparatus for bonding substrates comprises: pattern roll adapted to rotate about an axis of rotation extending in a first direction D, the pattern roll comprising an outer circumferential surface, the pattern roll comprising: a number, n, of continuous threads extending circumferentially around the axis of rotation along a helical path parallel with each other, wherein n is 2 or greater; wherein each thread protrudes radially outward from the outer circumferential surface; wherein each thread comprises first outer surfaces and second outer surfaces intermittently arranged circumferentially around the axis of rotation along a length of each thread; wherein the first outer surfaces are positioned radially outward from the axis of rotation by a first radius R1; wherein the second outer surfaces are positioned radially outward from the axis of rotation by a second radius R2 less than the first radius R1; wherein each first outer surface extends axially in the first direction, D, from a first edge to a second edge; wherein the first edges of neighboring threads are separated by a pitch length, PL, extending in the direction D; wherein the first edges of a first thread are separated from first edges of the first thread by a lead length, LL, extending in the direction D, wherein [LL=PL*n]; and wherein each thread comprises a helix angle, wherein

[helix angle=arctan((2*Π*R1)/(LL)), wherein 45°<helix angle<90° ]; and an anvil roll adjacent the pattern roll to define a nip between the first surfaces of the threads and the anvil roll.

In yet another form, a method for making an apparatus for bonding substrates comprises: providing a roll adapted to rotate about an axis of rotation extending in a first direction D; creating a plurality of grooves into the roll to form a number, n, of continuous threads extending circumferentially around the axis of rotation along a helical path parallel with each other, wherein n is 2 or greater, each thread comprising an outer circumferential surface extending axially in the first direction, D, from a first edge to a second edge; wherein the first edges of neighboring threads are separated by a pitch length, PL, extending in the direction D; wherein the first edges of a first thread are separated from first edges of the first thread by a lead length, LL, extending in the direction D, wherein [LL=PL*n]; and each thread comprising a helix angle, wherein

[helix angle=arctan((2*Π*R1)/(LL)), wherein
45°<helix angle<90°];

removing material from the outer circumferential surface of each thread to form discrete first outer surfaces and discrete second outer surfaces intermittently arranged circumferentially around the axis of rotation along a length of each thread; wherein the first outer surfaces are positioned radially outward from the axis of rotation by a first radius R1; wherein the second outer surfaces are positioned radially outward from the axis of rotation by a second radius R2 less than the first radius R1; and positioning an anvil adjacent the roll to define a nip between the first outer surfaces and the anvil.

BRIEF DESCRIPTION OF THE DRAWINGS

FIG. 1B is a plan view of the absorbent article of FIG. 1A that may include one or more patterned apertured substrates made in accordance with the present disclosure with the portion of the diaper that faces toward a wearer oriented towards the viewer.

FIG. 2A is a front perspective view of an absorbent article that may include one or more patterned apertured substrates made in accordance with the present disclosure.

FIG. 7 is a schematic representation of a front view of an example cross machine directional tensioning apparatus with outer longitudinal portions in an unexpanded and non-angled positions relative to a middle portion.

FIG. 8 is a schematic representation of a front view of the cross machine directional tensioning apparatus of FIG. 7 with the outer longitudinal portions in a longitudinally expanded position relative to the middle portion.

FIG. 9 is a schematic representation of a front view of the cross machine directional tensioning apparatus of FIG. 7 with the outer longitudinal portions in an angled and expanded position relative to the middle portion.

FIG. 10 is a schematic representation of a front view of a cross machine directional tensioning apparatus with outer longitudinal portions fixed in an angled position relative to a middle portion.

FIG. 11A is an isometric view of a roll.

FIG. 11B is an isometric view of the roll from FIG. 11A modified to include two relief channels.

FIG. 11C is an isometric view of the roll from FIG. 11B modified to include a first groove.

FIG. 11D is an isometric view of the roll from FIG. 11C modified to include a second groove to create a first thread between the first groove and the second groove.

FIG. 11E is an isometric view of the roll from FIG. 11D modified to include a third groove to create a second thread between the second groove and the third groove.

FIG. 11F is an isometric view of the roll from FIG. 11B modified to include a plurality of grooves and threads.

FIG. 15 is a detailed isometric view of a portion of a thread of the pattern roll from FIG. 14.

FIG. 16 is a top side view of the thread of the FIG. 15.

DETAILED DESCRIPTION OF THE INVENTION

Figure 1A:
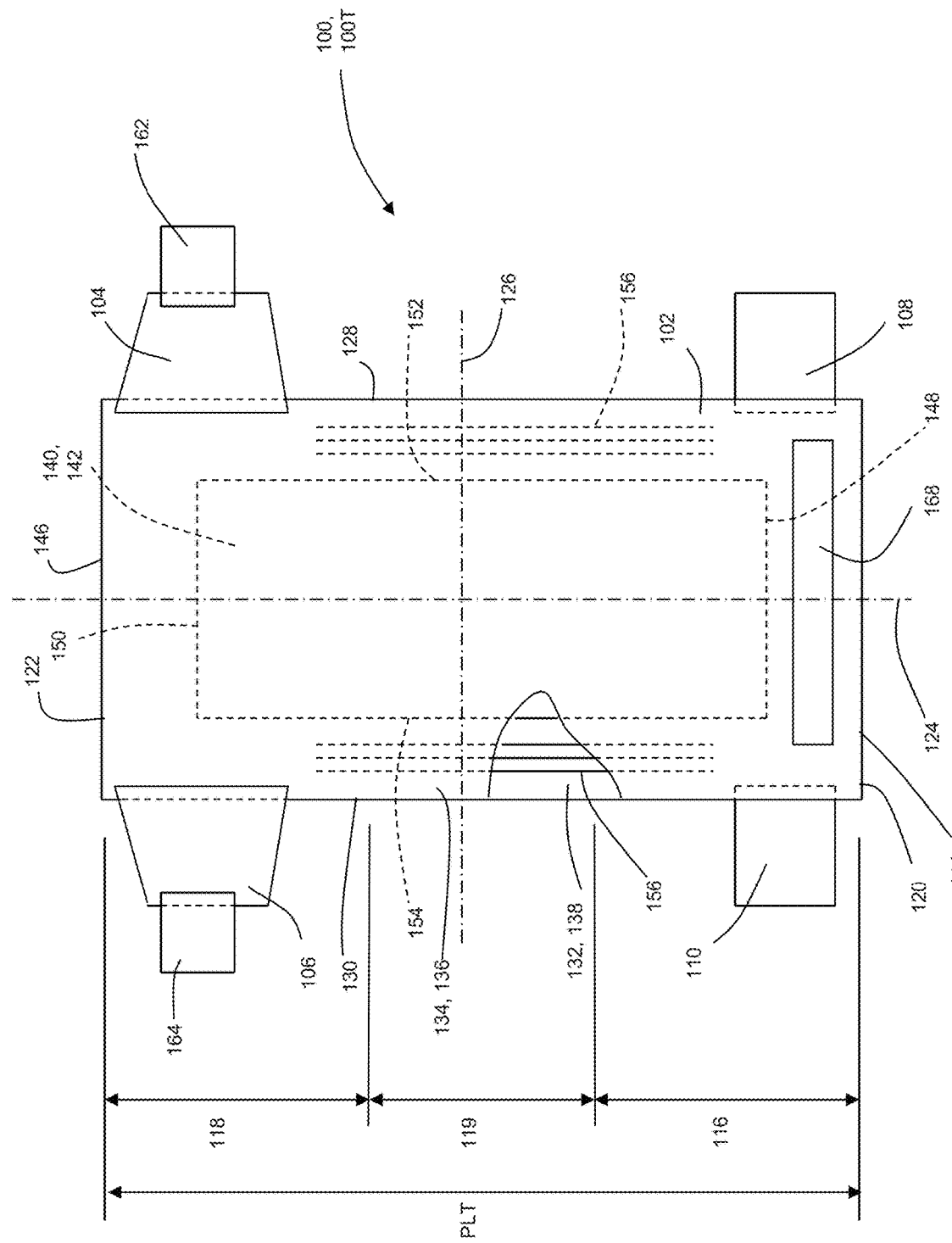
FIG. 1A is a partially cut away plan view of an absorbent article in the form of a taped diaper that may include one or more patterned apertured substrates made in accordance with the present disclosure with the portion of the diaper that faces away from a wearer oriented towards the viewer.

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner). The term "absorbent article" may also encompass cleaning or dusting pads or substrates that have some absorbency.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pullon diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

The term "feminine hygiene articles" refers to disposable absorbent articles used by women for catamenial protection. Such feminine hygiene articles may include sanitary napkins, tampons, interlabial products, incontinence devices, and pantiliners. Non-limiting examples of panty liners and sanitary napkins include those disclosed in U.S. Pat. Nos. 4,324,246; 4,463,045; 4,342,314; 4,556,146; 4,589,876; 4,687,478; 4,950,264; 5,009,653; 5,267,992; and 6,004,893.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof. Nonwovens do not have a woven or knitted filament pattern. It is to be appreciated that nonwovens having various basis weights can be used in accordance with the methods herein. For example, some nonwovens may have a basis weight of at least about 8 gsm, 12 gsm, 16 gsm, 20 gsm, 25 gsm, 25 gsm, 40 gsm, or 65 gsm. Some nonwovens may have basis weight of about 8 gsm to about 65 gsm, specifically reciting all 1 gsm increments within the above-recited ranges and all ranges formed therein or thereby.

It is to be appreciated that films having various basis weights can be used in accordance with the methods herein. For example, some films may have a basis weight of at least about 8 gsm, 12 gsm, 16 gsm, 20 gsm, 25 gsm, 25 gsm, 40 gsm, or 60 gsm. Some films may have basis weight of about 8 gsm to about 60 gsm, specifically reciting all 1 gsm increments within the above-recited ranges and all ranges formed therein or thereby.

The term "machine direction" (MD) is used herein to refer to the direction of material flow through a process. In addition, relative placement and movement of material can be described as flowing in the machine direction through a process from upstream in the process to downstream in the process.

The terms "cross direction" and "cross machine direction" (CD) are used herein to refer to a direction that is generally perpendicular to the machine direction.

As used herein, the term "aspect ratio" is the ratio of the major axis to the minor axis of a pattern surface, a bond region, or an aperture.

Aspects of the present disclosure relate to methods for manufacturing absorbent articles, and in particular, to apparatuses and methods for making patterned apertured substrates that may be used as components of absorbent articles. During the manufacturing processes herein, a precursor substrate advances in a machine direction between a pattern roll and an anvil roll. The pattern roll is adapted to rotate about an axis of rotation and includes a plurality of pattern surfaces, wherein the substrate is compressed between an outer circumferential surface of the anvil roll and the pattern surfaces of the pattern roll to form discrete bond regions in the substrate. The substrate is then stretched in a cross direction to cause the discrete bond regions to rupture and form apertures, wherein the cross direction is substantially perpendicular to the machine direction. As discussed in more detail below, the pattern surfaces on the pattern roll are formed on continuous threads that extend circumferentially around the axis of rotation along a helical path parallel with each other. As such, the pattern surfaces press the substrate against the outer circumferential surface of the anvil roll in different axial locations along the cross direction as the pattern roll rotates when forming the discrete bond regions. Because the pattern surfaces are arranged along helical paths around the pattern roll, the pattern surfaces exert pressure against the anvil roll at various locations along the axial length of the anvil roll, and in turn, help mitigate and/or reduce localized wear in the outer circumferential surface of the anvil roll that may otherwise occur.

It is to be appreciated that the systems and methods disclosed herein are applicable to work with various types of converting processes and/or machines, such as for example, absorbent article manufacturing and assembly processes, such as for example, described in U.S. Pat. No. 5,628,097 and U.S. Patent Publication Nos. 2003/0021951 A1 and 2016/0136014 A1. The methods and apparatuses are discussed below in the context of manufacturing diapers. And for the purposes of a specific illustration, FIGS. 1A and 1B show an example of an absorbent article 100 that may be assembled in accordance with the methods and apparatuses disclosed herein. In particular, FIG. 1A shows one example of a plan view of an absorbent article 100 configured as a taped diaper 100T, with the portion of the diaper that faces away from a wearer oriented towards the viewer. And FIG. 1B shows a plan view of the diaper 100 with the portion of the diaper that faces toward a wearer oriented towards the viewer. The taped diaper 100T shown in FIGS. 1A and 1B includes an absorbent chassis 102, first and second rear side panels 104 and 106; and first and second front side panels 108 and 110.

As shown in FIGS. 1A and 1B, the diaper 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The absorbent article may also include a laterally extending front waist edge 120 in the front waist region 116 and a longitudinally opposing and laterally extending back waist edge 122 in the back waist region 118. To provide a frame of reference for the present discussion, the diaper 100T in FIGS. 1A and 1B is shown with a longitudinal axis 124 and a lateral axis 126. The longitudinal axis 124 may extend through a midpoint of the front waist edge 120 and through a midpoint of the back waist edge 122. And the lateral axis 126 may extend through a midpoint of a first longitudinal or right side edge 128 and through a midpoint of a second longitudinal or left side edge 130.

As shown in FIGS. 1A and 1B, the diaper 100 includes an inner, body facing surface 132, and an outer, garment facing surface 134. And the chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs, an elastic waist region, and/or flaps, e.g., side panels and/or ears, to enhance the fits around the legs and waist of the wearer, to enhance the fit around the legs of the wearer.

As shown in FIGS. 1A and 1B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 1A, the laterally extending end edges 144 and 146 may form a portion of the laterally extending front waist edge 120 in the front waist region 116 and a portion of the longitudinally opposing and laterally extending back waist edge 122 in the back waist region 118. The distance between the first lateral end edge 144 and the second lateral end edge 146 may define a pitch length, PLT, of the chassis 102. When the diaper 100 is worn on the lower torso of a wearer, the front waist edge 120 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper 100 may also include an absorbent assembly 140 that is joined to the chassis 102. As shown in FIGS. 1A and 1B, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

As previously mentioned, the diaper 100 may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1.

The elasticized waistband 158 may provide improved fit and containment and may be a portion or zone of the diaper 100 that may elastically expand and contract to dynamically fit a wearer's waist. The elasticized waistband 158 may extend longitudinally inwardly from the waist edges 120, 122 of the diaper toward the lateral edges 148, 150 of the absorbent core 142. The diaper 100 may also include more than one elasticized waistband 158, for example, having one waistband 158 positioned in the back waist region 118 and one waistband 158 positioned in the front wait region 116, although other embodiments may be constructed with a single elasticized waistband 158. The elasticized waistband 158 may be constructed in a number of different configurations including those described in U.S. Pat. Nos. 4,515,595 and 5,151,092. In some embodiments, the elasticized waistbands 158 may include materials that have been "pre-strained" or "mechanically prestrained" (subjected to some degree of localized pattern mechanical stretching to permanently elongate the material). The materials may be pre-strained using deep embossing techniques as are known in the art. In some embodiments, the materials may be pre-strained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107,364; 4,209,563; 4,834,741; and 5,151,092.

As shown in FIG. 1B, the chassis 102 may include longitudinally extending and laterally opposing side flaps 160 that are disposed on the interior surface 132 of the chassis 102 that faces inwardly toward the wearer and contacts the wearer. Each side flap may have a proximal edge. The side flaps may also overlap the absorbent assembly 140, wherein the proximal edges extend laterally inward of the respective side edges of the absorbent assembly 152 and 154. In some configurations, the side flaps may not overlap the absorbent assembly. It is to be appreciated that the side flaps may be formed in various ways, such as for example, by folding portions of the chassis 102 laterally inward, i.e., toward the longitudinal axis 124, to form both the respective side flaps and the side edges 128 and 130 of the chassis 102. In another example, the side flaps may be formed by attaching an additional layer or layers to the chassis at or adjacent to each of the respective side edges and of the chassis. Each of the side flaps may be joined to the interior surface 132 of the chassis and/or the absorbent assembly in side flap attachment zones in the front waist region 116 and in side flap attachment zones in the back waist region 118. The side flaps may extend to the same longitudinal extent as the absorbent article or alternatively the side flaps may have a longitudinal extent that is less than the absorbent article.

Taped diapers may be manufactured and provided to consumers in a configuration wherein the front waist region and the back waist region are not fastened, pre-fastened, or connected to each other as packaged, prior to being applied to the wearer. For example, the taped diaper 100 may be folded about a lateral centerline with the interior surface 132 of the first waist region 116 in surface to surface contact with the interior surface 132 of the second waist region 118 without fastening or joining the waist regions together. The rear side panels 104 and 106 and/or the front side panels 108 and 110 may also be folded laterally inward toward the inner surfaces 132 of the waist regions 116 and 118.

The diaper 100 may also include various configurations of fastening elements to enable fastening of the front waist region 116 and the back waist region 118 together to form a closed waist circumference and leg openings once the diaper is positioned on a wearer. For example, as shown in FIGS. 1A and 1B, the diaper 100 may include first and second fastening members 162, 164, also referred to as tabs, connected with the first and second rear side panels 104, 106, respectively. The diaper may also include first and second front side panels 108, 110, that may or may not include fastening members.

With continued reference to FIGS. 1A and 1B, each side panel 104, 106 and/or fastening member 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening members 162, 164 may form a portion of or may be permanently bonded, adhered or otherwise joined directly or indirectly to the first and second rear panels 104, 106 at or adjacent the distal edge of the panel and/or the first and second front side panels 108 and 110 at or adjacent the distal edge of the side panel. It is to be appreciated that the fastening members and/or side panels may be assembled in various ways, such as disclosed for example, in U.S. Pat. No. 7,371,302. The fastening members 162, 164 and/or side panels 104, 106, 108, 110 may also be permanently bonded or joined at or adjacent the side edges 128 and 130 of the chassis 102 in various ways, such as for example, by adhesive bonds, sonic bonds, pressure bonds, thermal bonds or combinations thereof, such as disclosed for example, U.S. Pat. No. 5,702,551.

Referring now to FIG. 1B, the first fastening member 162 and/or the second fastening member 164 may include various types of releasably engageable fasteners. The first and second fastening members 162 and/or 164 may also include various types of refastenable fastening structures. For example, the first and second fastening members 162 and 164 may include mechanical fasteners, 166, in the form of hook and loop fasteners, hook and hook fasteners, macro-fasteners, buttons, snaps, tab and slot fasteners, tape fasteners, adhesive fasteners, cohesive fasteners, magnetic fasteners, hermaphroditic fasteners, and the like. Some examples of fastening systems and/or fastening members 162, 164 are discussed in U.S. Pat. Nos. 3,848,594; 4,662,875; 4,846, 815; 4,894,060; 4,946,527; 5,151,092; 5,221,274; 6,251, 097; 6,669,618; 6,432,098; and U.S. Patent Publication Nos. 2007/0078427 A1 and 2007/0093769 A1.

As previously mentioned, the fastening members 162 and 164 may be constructed from various materials and may be constructed as a laminate structure. The fastening members 162 and 164 may also be adapted to releasably and/or refastenably engage or connect with another portion of the diaper 100. For example, as shown in FIG. 1A, the diaper 100 may include a connection zone 168, sometimes referred to as a landing zone, in the first waist region 116. As such, when the taped diaper 100 is placed on a wearer, the fastening members 162 and 164 may be pulled around the waist of the wearer and connected with the connection zone 168 in the first waist region 116 to form a closed waist circumference and a pair of laterally opposing leg openings. It is to be appreciated that the connection zone may be constructed from a separate substrate that is connected with the chassis 102 of the taped diaper. In some embodiments, the connection zone may be integrally formed as part of the backsheet 136 of the diaper 100 or may be formed as part of the first and second front panels 108, 110, such as described in U.S. Pat. Nos. 5,735,840 and 5,928,212.

Figure 2C:
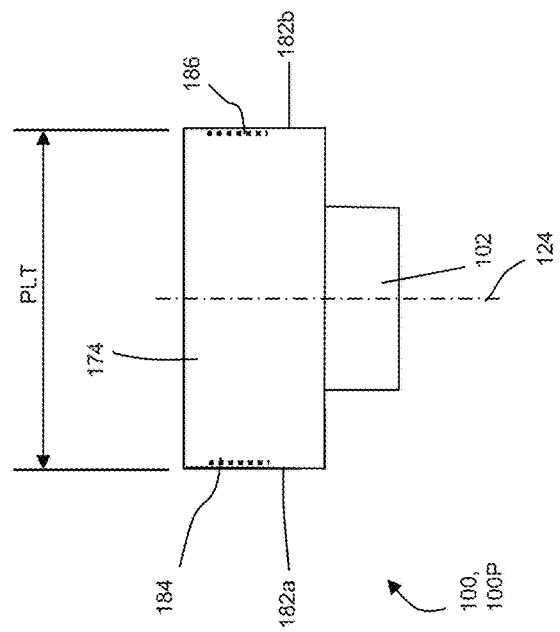
FIG. 2C is a rear view of the absorbent article of FIG. 2A.
Figure 2B:
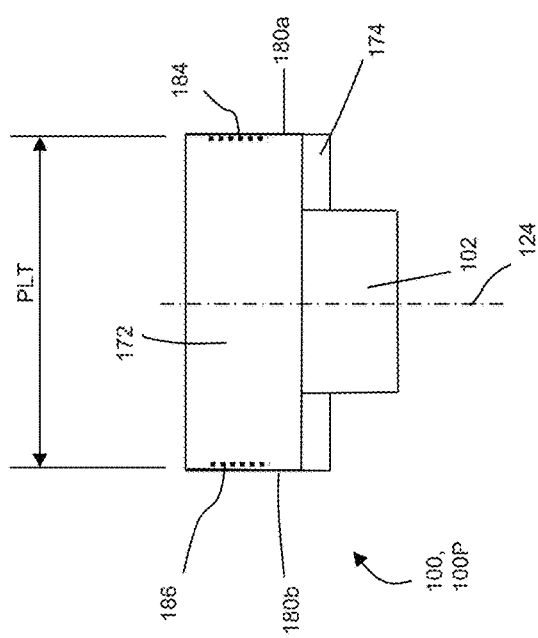
FIG. 2B is a front view of the absorbent article of FIG. 2A.

As previously mentioned, absorbent articles 100 may also be configured as diaper pants 100P having a continuous perimeter waist opening and continuous perimeter leg openings. For example, FIG. 2A shows a perspective view of an absorbent article 100 in the form of a diaper pant 100P in a pre-fastened configuration, and FIGS. 2B-2C show front and rear plan views of the diaper pant 100P. The diaper pant 100P may include a chassis 102 such a discussed above with reference to FIG. 1A and a ring-like elastic belt 170 such as shown in FIG. 2A. In some embodiments, a first elastic belt 172 and a second elastic belt 174 are bonded together to form the ring-like elastic belt 170. As such, diaper pants may be manufactured with the ring-like elastic belt 174 and provided to consumers in a configuration wherein the front waist region 116 and the back waist region 118 of the chassis 102 are connected to each other as packaged, prior to being applied to the wearer. As such, diaper pants may have a continuous perimeter waist opening 176 and continuous perimeter leg openings 178 such as shown in FIG. 2A.

As previously mentioned, the ring-like elastic belt 170 may be defined by a first elastic belt 172 connected with a second elastic belt 174. As shown in FIGS. 2A-2C, the first elastic belt 172 extends between a first longitudinal side edge 180a and a second longitudinal side edge 180b. And the second elastic 174 belt extends between a first longitudinal side edge 182a and a second longitudinal side edge 182b. The distance between the first longitudinal side edge 180a and the second longitudinal side edge 180b defines a pitch length, PLT, of the first elastic belt 172, and the distance between the first longitudinal side edge 182a and the second longitudinal side edge 182b defines the pitch length, PLT, of the second elastic belt 174. The first elastic belt is connected with the first waist region 116 of the chassis 102, and the second elastic belt 108 is connected with the second waist region 116 of the chassis 102. As shown in FIGS. 2A-2C, opposing end regions of the first elastic belt 172 are connected with opposing end regions of the second elastic belt 174 at a first side seam 184 and a second side seam 186 to define the ring-like elastic belt 170 as well as the waist opening 176 and leg openings 178. It is to be appreciated that the ring-like elastic belt may be formed by joining a first elastic belt to a second elastic belt with permanent side seams or with openable and reclosable fastening systems disposed at or adjacent the laterally opposing sides of the belts.

As previously mentioned, absorbent articles may be assembled with various components that may constructed with the patterned apertured substrates described herein. Thus, in the context of the previous discussion, the apparatuses and methods herein may be used to make patterned apertured substrates configured as continuous substrates and/or discrete components of an absorbent article 100. For example, the apparatuses and methods herein may be utilized to create patterned apertured substrates to be used as or with any of the topsheet 138; backsheet 136; absorbent core 140; leg cuffs 156; waist feature 158; side panels 104, 106, 108, 110; connection zones 168; fastening elements 162, 164, 166, and/or belts of an absorbent article 100. In additional examples, the apparatuses and methods herein may be utilized to create patterned apertured substrates to be used as or with various components and absorbent articles described in U.S. Patent Publication No. 2016/0136014 A1.

It is to be appreciated that the systems and methods disclosed herein are applicable to work with various types of converting processes and/or machines. The patterned apertured substrates of the present disclosure may be made generally by using the process generally described in U.S. Pat. No. 5,628,097 and U.S. Patent Publication Nos. 2003/ 0021951 A1 and 2016/0136014 A1. For example, FIG. 3 shows a schematic representation of a converting apparatus 200 configured to form a patterned apertured substrate 300 from a precursor substrate 302, also referred to herein as a precursor material, advancing in a machine direction MD through the converting apparatus 200.

Figure 3:
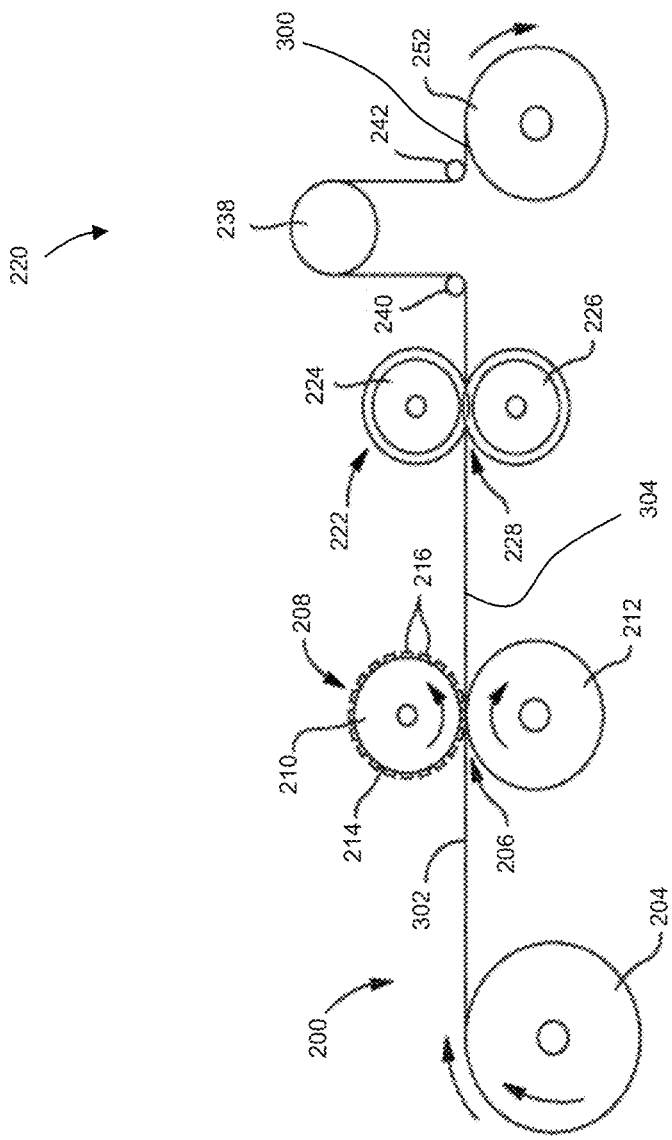
FIG. 3 is a schematic representation of an apparatus for producing patterned apertured substrates.

With continued reference to FIG. 3, a precursor material 302 is supplied to the apparatus 200 as the starting material. The precursor material 302 can be supplied as discrete webs, such as for example, sheets or patches of material for batch processing. For commercial processing, the precursor material 302 may be supplied as roll stock, and as such, may be considered as having a finite width and an infinite length. In such a context, the length is measured in the machine direction (MD), and the width is measured in the cross direction (CD).

The precursor material may be configured in various ways. For example, the precursor material 302 may be one or more nonwoven materials (same or different), one or more films (same or different), a combination of one or more nonwoven materials and one or more films, or any other suitable materials or combinations thereof. The precursor material 302 may be purchased from a supplier and shipped to where the patterned apertured substrates are being formed or the precursor material 302 formed at the same location as where the patterned apertured substrates are being produced. The precursor material 302 may be extensible, elastic, or nonelastic. Further, the precursor material 302 may be a single layer material or a multilayer material. In an instance, the precursor material 302 may be joined to a polymeric film to form a laminate.

The precursor material 302 may comprise or be made of mono-component, bi-component, multi-constituent blends, or multi-component fibers comprising one or more thermoplastic polymers. For example, the bicomponent fibers of the present disclosure may be formed of a polypropylene core and a polyethylene sheath. Further details regarding bi-component or multi-component fibers and methods of making the same may be found in U.S. Patent Publication No. 2009/0104831 A1 and U.S. Pat. Nos. 8,226,625; 8,226,626; 8,231,595; and 8,388,594. The various fibers may be sheath/core, side-by-side, islands in the sea, or other known configurations of fibers. The fibers may be round, hollow, or shaped, such as trilobal, ribbon, capillary channel fibers, such as 4DG. The fibers may comprise microfibers or nanofibers.

Figure 4:
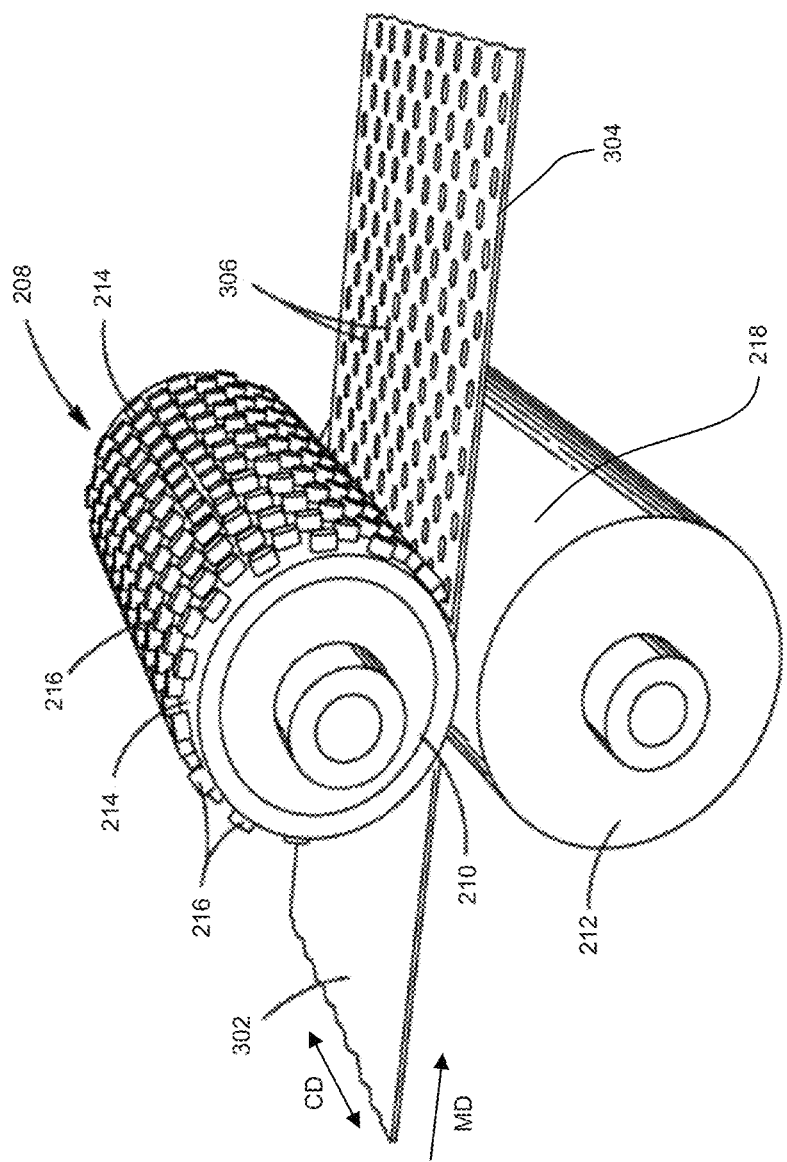
FIG. 4 is a perspective view of a weakening roller arrangement of FIG. 3.

The precursor material 302 may be unwound from a supply roll 204 and advanced in a direction indicated by the arrow associated therewith as the supply roll 204 rotates in the direction indicated by the arrow associated therewith. From the supply roll 204, the precursor material 302 advances through a nip 206 defined in a weakening roller (or overbonding) arrangement 208, thereby forming a weakened precursor material 304, also referred to herein as a weakened precursor substrate. As shown in FIG. 4, the weakened precursor material 304 includes a pattern of discrete bond regions 306 after advancing through the nip 206. The discrete bond regions 306 are also referred to herein as overbonds; densified and weakened areas; and weakened, melt stabilized locations. As discussed in further detail below, the weakened precursor material 304 may be stretched in the cross direction CD, or generally in the CD, by a cross directional tensioning force to at least partially, or fully, rupture the plurality of weakened, melt stabilized locations 306 to form the patterned aperture substrate 300.

Referring now to FIGS. 3 and 4, the weakening roller arrangement 208 may comprise a pattern roll 210, also referred to herein as a patterned calendar roller, and an anvil roll 212. One or both of the pattern roll 210 and the anvil roll 212 may be heated and the pressure between the two rolls may be adjusted by known techniques to provide the desired temperature, if any, and pressure to concurrently weaken and melt-stabilize ("overbond") the precursor material 202 at a plurality of discrete bond regions 306, also referred to herein as weakened, melt stabilized locations. In some configurations, the temperature of the pattern roll 210 (or portions thereof) and/or the anvil roll 212 (or portions thereof) may be ambient temperature or may be in the range of about 100° C. to about 300° C., about 100° C. to about 250° C., about 100° C. to about 200° C., or about 100° C. to about 150° C., specifically reciting all 0.5° C. increments within the specified ranges and all ranges formed therein or thereby. The pressure between the pattern roll 210 and the anvil roll 212 may be in the range of about 2,000 pli (pounds per linear inch) to about 10,000 pli, about 3,000 pli to about 8,000 pli, or about 4,500 to about 6,500 pli, specifically reciting all 0.1 pli increments within the specified ranges and all ranges formed therein or thereby.

As shown generally in FIGS. 3 and 4, the pattern roll 210 may include an outer circumferential surface 214 and a plurality of pattern surfaces 216 positioned radially outward from the outer circumferential surface 214. During operation, the precursor substrate 302 advances between pattern roll 210 and the anvil roll 212 such that the precursor substrate 302 is compressed between the anvil roll 212 and the pattern surfaces 216 to form discrete bond regions 306 in the weakened precursor substrate 304. It is to be appreciated that the pattern surfaces 216 of the pattern roll 210 are illustrated in FIGS. 3 and 4 as a simplified example, and a more detailed description of pattern rolls 210 and associated pattern surfaces 216 that can be used to produce patterned apertured substrates 300 of the present disclosure are discussed below with reference to additional figures. The pattern surfaces 216 may be disposed in a predetermined pattern with each of the pattern surfaces 216 being configured and disposed to precipitate a weakened, melt-stabilized location in the precursor material 302 to affect a predetermined pattern of weakened, melt-stabilized locations 306 in the precursor material 302. The pattern surfaces 216 may have a one-to-one correspondence to the pattern of melt stabilized locations 306 in the weakened precursor material 304. As shown in FIG. 4, the pattern roll 210 may have a repeating pattern of the pattern surfaces 216 which extend about the entire circumference of surface 214. In some configurations, the pattern surfaces 216 may extend around a portion, or portions of the circumference of the surface 214. The anvil roll 212 may also be configured in various ways. For example, as shown in FIG. 4, the anvil roll 212 may include an outer circumferential surface 218 defining a smooth surfaced, circular cylinder of steel, rubber, or other material. The anvil roll 212 and the pattern roll 210 may be positioned differently relative each other than the positions shown in FIG. 4, for example, wherein the anvil roll 212 is positioned above or to the right or left of the pattern roll 210 and achieve the same result.

It is to be appreciated that the pattern rolls 210 and anvil rolls 212 herein may be made from various materials. For example, in some configurations, the pattern roll 210 and/or anvil roll 212 may be made from hardened tool steel, powder metal tool steel, or tungsten carbide.

It is to be appreciated that the weakening roller arrangement 208 may be configured in various ways. For example, the weakening roller arrangement may comprise a pattern roll and an ultrasonic bonding device including an ultrasonic horn, wherein the precursor substrate 302 advances between the pattern roll and an ultrasonic horn to form discrete bond regions 306 in the weakened precursor substrate 304. It is to be appreciated that aspects of the ultrasonic bonding devices may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device may be configured as a linear oscillating type sonotrode, such as for example, available from Herrmann Ultrasonic, Inc. In some configurations, the sonotrode may include a plurality of sonotrodes nested together in the cross direction CD.

Figure 5:
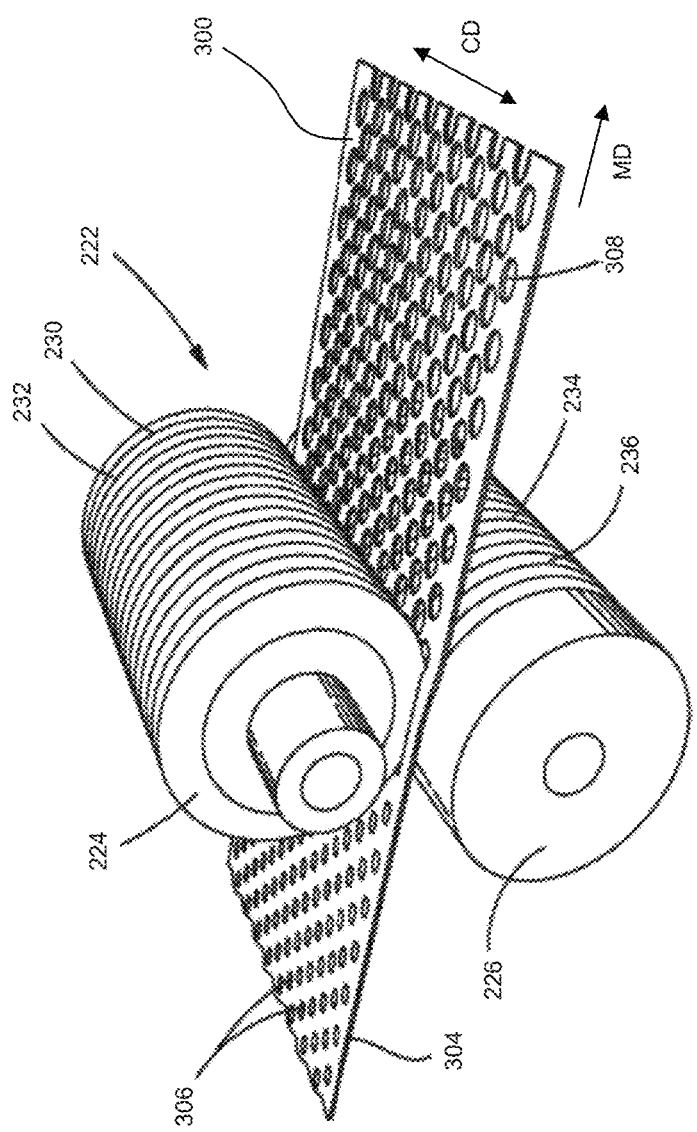
FIG. 5 is a perspective view of an incremental stretching system of FIG. 3.
Figure 6:
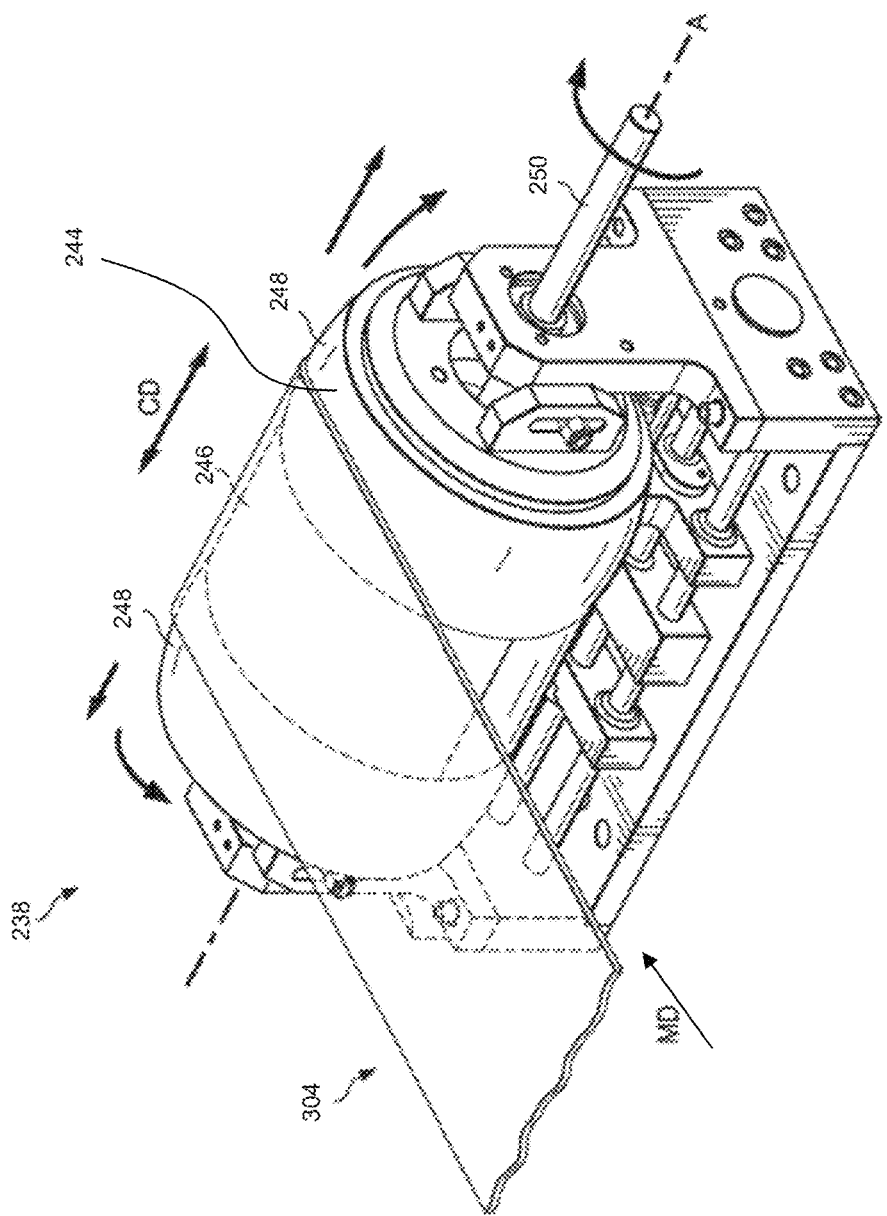
FIG. 6 is a perspective view of an example cross machine directional tensioning apparatus of FIG. 3.

Referring now to FIGS. 3, 5, and 6, the weakened precursor material 304 advances from the weakening roller arrangement 208 to a stretching system 220 wherein the weakened precursor material 304 may be stretched in the cross direction CD, or generally in the CD, by cross directional tensioning forces to at least partially, or fully, rupture the plurality of weakened, melt stabilized locations 306, thereby creating a plurality of at least partially formed apertures 308 in the precursor material 102 coincident with the plurality of weakened, melt stabilized locations 306. As such, at least some or all of the discrete bond regions 306 are used to form apertures 308 in the weakened precursor material 304. In turn, the patterns of discrete bond regions 306 may correlate generally with the patterns of apertures 308 created in the weakened precursor material 304.

As shown in FIGS. 3 and 5, the stretching system 220 may include an include an incremental stretching apparatus 222 including opposed pressure applicators having three-dimensional surfaces that may at least to a degree may be complementary to one another. FIG. 5 shows a fragmentary enlarged view of an incremental stretching apparatus 222 comprising a first incremental stretching roller 224 positioned adjacent a second incremental stretching roller 226 to define a nip 228 therebetween. The first incremental stretching roller 224 may comprise a plurality of teeth 230 and corresponding grooves 232 which may extend about the entire circumference of first incremental stretching roller 224. The second incremental stretching roller 226 may comprise a plurality of teeth 234 and a plurality of corresponding grooves 236. The teeth 230 on the first roller 224 may be configured to intermesh with or engage the grooves 236 on the second roller 226 while the teeth 234 on the second roller 226 may be configured to intermesh with or engage the grooves 232 on the first roller 224. The spacing of the teeth 230, 234 and/or the grooves 232, 236 may be configured to match the spacing of the plurality of weakened, melt stabilized locations 306 in the weakened precursor material 304 or may be smaller or larger.

As the weakened precursor material 304 advances through the nip 228 of the incremental stretching apparatus 222, the weakened precursor material 304 is subjected to tensioning in the cross direction CD, causing the weakened precursor material 304 to be extended (or activated) in the cross direction CD, or generally in the cross direction CD. Additionally, the weakened precursor material 304 may be tensioned in the machine direction MD, or generally in the machine direction MD. The cross direction CD tensioning force exerted on the weakened precursor material 304 may be adjusted such that the weakened, melt-stabilized locations 306 at least partially or fully rupture, thereby creating a plurality of partially formed or formed apertures 308 coincident with the weakened melt-stabilized locations. However, other bonds of the weakened precursor material 306 (in the non-overbonded areas) may be strong enough such that these regions do not rupture during tensioning, thereby maintaining the weakened precursor material 306 in a coherent condition even as the weakened, melt-stabilized locations 306 rupture. However, it may be desirable to have some of the bonds rupture during tensioning. It is to be appreciated that the incremental stretching apparatus may be configured in various ways, such as disclosed in U.S. Patent Publication No. 2016/0136014 A1.

In some configurations, the stretching system 220 may include a cross directional tensioning apparatus 238, such as shown in FIGS. 3 and 6. For example, weakened precursor material 304 may advance from the incremental web stretching apparatus 208 to and at least partially around the cross machine directional tensioning apparatus 238. As shown in FIG. 3, the cross machine directional tensioning apparatus 238 may be offset from the main processing line by running the weakened precursor material 304 partially around idlers 240 and 242 or stationary bars, for example. In some configurations, the cross machine tensioning apparatus 238 may be positioned in line with the main processing line.

As shown in FIG. 6, the cross machine directional tensioning apparatus 238 may comprise a roll 244 that comprises at least one outer longitudinal portion that expands along a longitudinal axis, A, of the roll, relative to a middle portion of the roll 244, to stretch and/or expand the weakened precursor material 304 in the cross machine direction CD. Instead of or in addition to expanding along the longitudinal axis, A, of the roll 244, the outer longitudinal portion may be angled relative to the longitudinal axis, A, of the roll 244 in a direction away from the weakened precursor material 304 being advanced over the roll 244 to stretch the weakened precursor material 304 in the cross machine direction CD or generally in the cross machine direction CD. In some configurations, the roll 244 may comprise two outer longitudinal portions that may expand in opposite directions generally along the longitudinal axis, A, of the roll 244. The two outer portions may both be angled downwards in a direction away from the weakened precursor material 304 being advanced over the roll 244. Such movement or positioning of the outer longitudinal portions of the roll 244 allows for generally cross machine directional tensioning of the weakened precursor material 304, which causes the plurality of weakened locations 306 to rupture and/or be further defined or formed into apertures 308.

The outer longitudinal portions of the roll 244 may comprise vacuum, a low tack adhesive, a high coefficient of friction material or surface, such as rubber, and/or other mechanisms and/or materials to hold the weakened precursor material 304 to the outer lateral portions of the roll 244 during movement of the outer longitudinal portion or portions relative to the middle portion of the roll. The vacuum, low tack adhesive, high coefficient of friction material or surface, and/or other mechanisms and/or materials may prevent, or at least inhibit, the held portions of the weakened precursor material 304 from slipping relative to the longitudinal axis, A, of the roll 244 during stretching of the outer lateral portions of the material in the cross machine direction or generally in the cross machine direction.

FIG. 6 is a top perspective view of the example cross machine directional tensioning apparatus 238. The cross machine directional tensioning apparatus 238 may comprise a roll 244 comprising a middle portion 246 and two outer longitudinal portions 248 situated on either end of the middle portion 246. The roll 244 may rotate about its longitudinal axis, A, on a drive shaft 250. The roll may rotate relative to the drive shaft 250 or in unison with the drive shaft 250, as will be recognized by those of skill in the art. The weakened precursor material 304 may be advanced over the entire cross machine directional width of the middle portion 246 and at least portions of the cross machine directional widths of the outer longitudinal portions 248. In some configurations, the weakened precursor material 304 may be advanced over at least about 5% up to about 80% of the circumference of the roll 244 so that the cross machine directional stretching may be performed.

FIG. 7 is a schematic representation of a front view of an example cross machine directional tensioning apparatus 238 with outer longitudinal portions 248 in an unexpanded or non-angled position relative to the middle portion 246. FIG. 8 is a schematic representation of a front view of the cross machine directional tensioning apparatus 238 of FIG. 7 with the outer longitudinal portions 248 in a longitudinally expanded position relative to the middle portion 246. FIG. 9 is a schematic representation of a front view of the cross machine directional tensioning apparatus 238 of FIG. 7 with the outer longitudinal portions 248 in an angled and expanded position relative to the middle portion 246. In regard to FIG. 9, the outer longitudinal portions 248 may merely move or slide in a direction generally perpendicular to the machine direction MD of the weakened precursor material 304 passing over the roll 244 to apply the cross machine directional tensioning force to the weakened precursor material 304. FIG. 10 is a schematic representation of a front view of a cross machine directional tensioning apparatus 238 with the outer longitudinal portions 248 fixed in an angled position relative to the middle portion 246 to apply the cross machine directional tensioning force to the weakened precursor material 304. In such a form, the middle portion 246 and each of the outer longitudinal portions 248 may comprise separate rolls.

Regardless of whether one or both of the outer longitudinal portions 248 is moved, slid, rotated, fixed, and/or expanded relative to the middle portion 246, this relative motion or positioning between the outer longitudinal portions 248 and the middle portion 246 stretches the weakened precursor material 304 in a cross machine direction CD to further rupture or further define the bond regions 306 in the weakened precursor material 304 and create, or further form, a plurality of the apertures 308 to form the patterned apertured substrate 300. In some configurations, the cross machine directional tensioning force applied by the cross machine directional tensioning apparatus 238 may be, for example, 10-25 grams or 15 grams. In some configurations, the cross machine directional tensioning apparatus 238 may be similar to, or the same as, the incremental stretching apparatus 222 to apply the cross machine directional tensioning forces. In still other configurations, any suitable cross machine directional tensioning apparatus may be used to apply the cross machine directional tensioning force to the weakened precursor material 304 to form the patterned apertured substrate 300.

In some configurations, the incremental stretching step or the cross machine directional stretching step described herein may be performed at elevated temperatures. For example, the weakened precursor material 304, the incremental stretching apparatus 222 and/or the cross directional tensioning apparatus 238 may be heated. Utilizing heat in the stretching step may soften the weakened precursor material 304, and may help the fibers therein extend without breaking.

One of ordinary skill in the art will recognize that it may be advantageous to submit the weakened precursor material 304 to multiple incremental stretching processes depending on various desired characteristics of the finished product. Both the first and any additional incremental stretching may either be done on-line or off-line. Furthermore, one of ordinary skill will recognize that the incremental stretching may be done either over the entire area of the material or only in certain regions of the material depending on the final desired characteristics. Referring again to FIG. 3, the patterned apertured substrate 300 may be taken up on wind-up roll 252 and stored. In some configurations, the patterned apertured substrate 300 may be fed directly to a production line where it is used to form a portion of an absorbent article or other consumer product. It is to be appreciated that in some scenarios, the overbonding step illustrated in FIGS. 3 and 4 could be performed by a material supplier and the weakened precursor material may be shipped to a consumer product manufacturer to perform the cross directional stretching steps. In some scenarios, the overbonding step may be used in a nonwoven production process to form overbonds, which may be in addition to, or in lieu of, primary bonds formed in the nonwoven production process. In some scenarios, a material supplier may fully perform the overbonding and stretching steps illustrated in FIG. 3 and then the patterned apertured substrate 300 may be shipped to the consumer product manufacturer. The consumer product manufacturer may also perform all of the steps in FIG. 3 after obtaining a precursor substrate 302 from a material supplier.

As discussed above, when forming a patterned apertured substrate 300, a precursor substrate 302 advances between the pattern roll 210 and the anvil roll 212 such that the precursor substrate 302 is compressed between the anvil roll 212 and the pattern surfaces 216 to form discrete bond regions 306 in the weakened precursor substrate 304. The pattern surfaces 216 may have a one-to-one correspondence to the pattern of discrete bond regions 306 in the weakened precursor material 304. The weakened precursor material 304 is then stretched in the cross direction CD to rupture the bond regions 306 to form a patterned apertured substrate 300 having a plurality of apertures 308 that may be coincident with the plurality of discrete bond regions 306.

As previously mentioned, the pattern rolls 210 herein may be configured to help mitigate and/or reduce localized wear in the outer circumferential surface of the anvil roll that may otherwise occur. For example, the pattern surfaces 216 may be arranged along helical paths around the pattern roll 210 such that the pattern surfaces 216 exert pressure against outer circumferential surface 218 of the anvil roll 212 at various locations along the axial length of the anvil roll 212 during operation. It is to be appreciated that the pattern rolls 210 with pattern surfaces 216 arranged in helical paths may be constructed in various ways. For example, FIGS. 11A-11F show an example progression of a method for making pattern rolls 210 according to the present disclosure.

As shown in FIG. 11A, a roll 400 having a first outer circumferential surface 402 defining a cylindrical shape may be provided, wherein the roll 400 is adapted to rotate about an axis of rotation 404 extending in a direction Dir. The first outer circumferential surface 402 may be positioned radially outward from the axis of rotation 404 by a first radius R1. During operation, the direction Dir may be the same as the cross direction CD. It to be appreciated that the roll of FIG. 11A may be provided in various ways. For example, the roll 400 may be provided from a forging. In another example, the roll 400 may be provided by heat shrinking a sleeve onto an outer surface of a shaft.

As shown in FIG. 11B, the roll 400 of FIG. 11A may be modified by creating relief channels 406 adjacent at opposing axial end portions of the roll 400. As discussed below with reference to FIGS. 11C-11F, the roll 400 of FIG. 11B may be further modified by creating a number, m, of grooves 3000 in the roll 400 to form a number, n, of continuous independent threads 5000 extending circumferentially around the axis of rotation 404 along a helical path parallel with each other. For example, as shown in FIG. 11C, the roll 400 of FIG. 11B may be further modified by creating a first groove 3001 in the first outer circumferential surface 402 the roll 400. And as shown in FIG. 11D, the roll 400 of FIG. 11C may be further modified by creating a second groove 3002 in first outer circumferential surface 402 the roll 400, such that a first thread 5001 is defined between the first groove 3001 and the second groove 3002. With continued reference to FIG. 11E, the roll 400 of FIG. 11D may be further modified by creating a third groove 3003 in first outer circumferential surface 402 the roll 400, such that a second thread 5002 is defined between the second groove 3002 and the third groove 3003. It is to be appreciated that the grooves 3000 may be formed in various ways. For example, grooves 3000 may be created by grinding material from the roll 400.

As shown in FIG. 11F, the process of creating grooves 3000 to form threads 5000 may be repeated such that a number, m, of grooves 3001-300m may form a number, n, of threads 5001-500n on the roll 400. It is to be appreciated that various numbers of grooves 3000 may be used to form various numbers of independent threads 5000 on the roll 400, such that number of threads, n, is 2 or greater. In addition, the number of grooves, m, may be equal to n+1. In some configurations, the number of independent threads, n, is greater than 2 and less than 25, specifically reciting all 1 thread increments within the specified ranges and all ranges formed therein or thereby.

Figure 12:
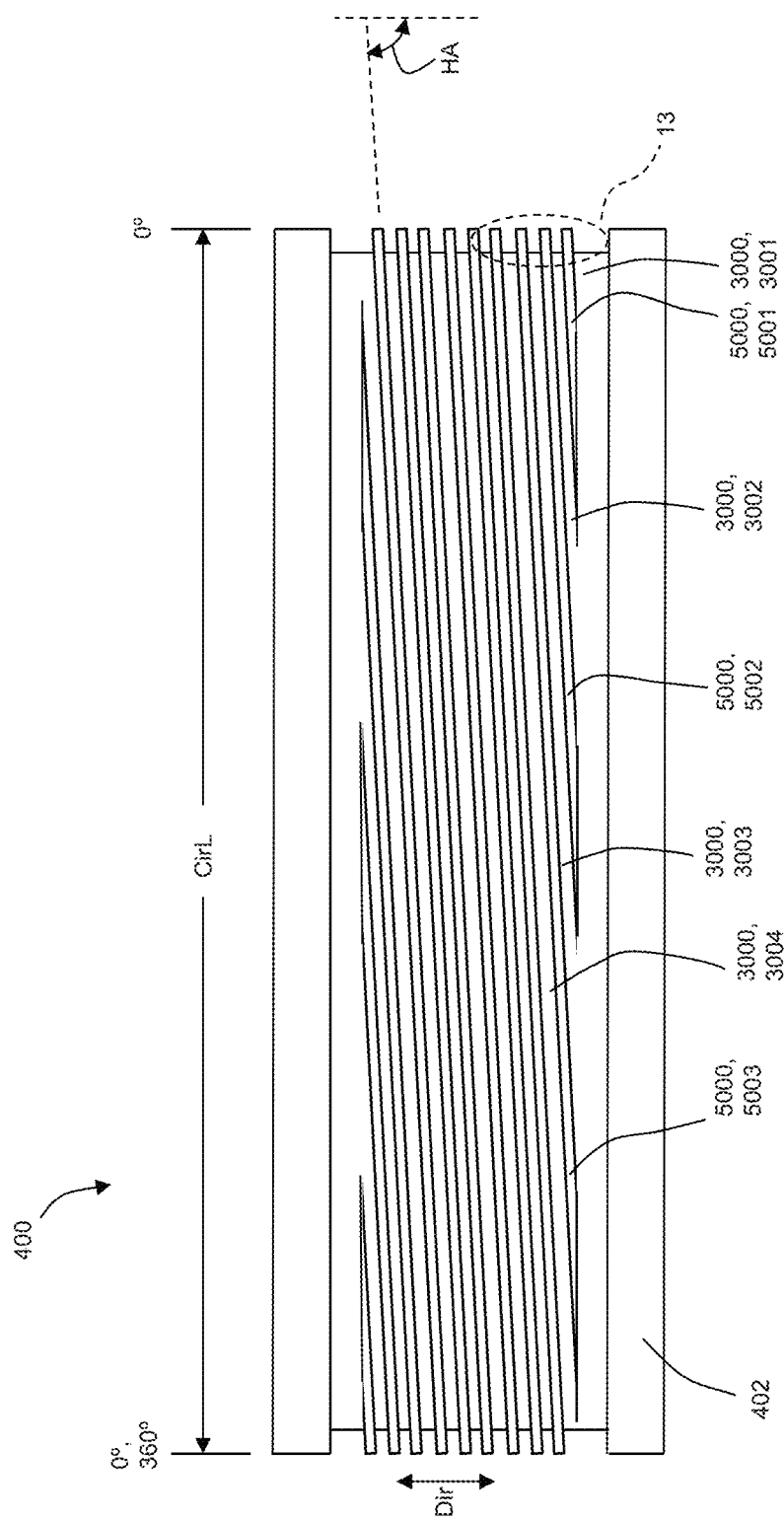
FIG. 12 is a laid out flat view of an outer circumferential surface of the roll shown in FIG. 11B modified to include three independent threads.
Figure 13:
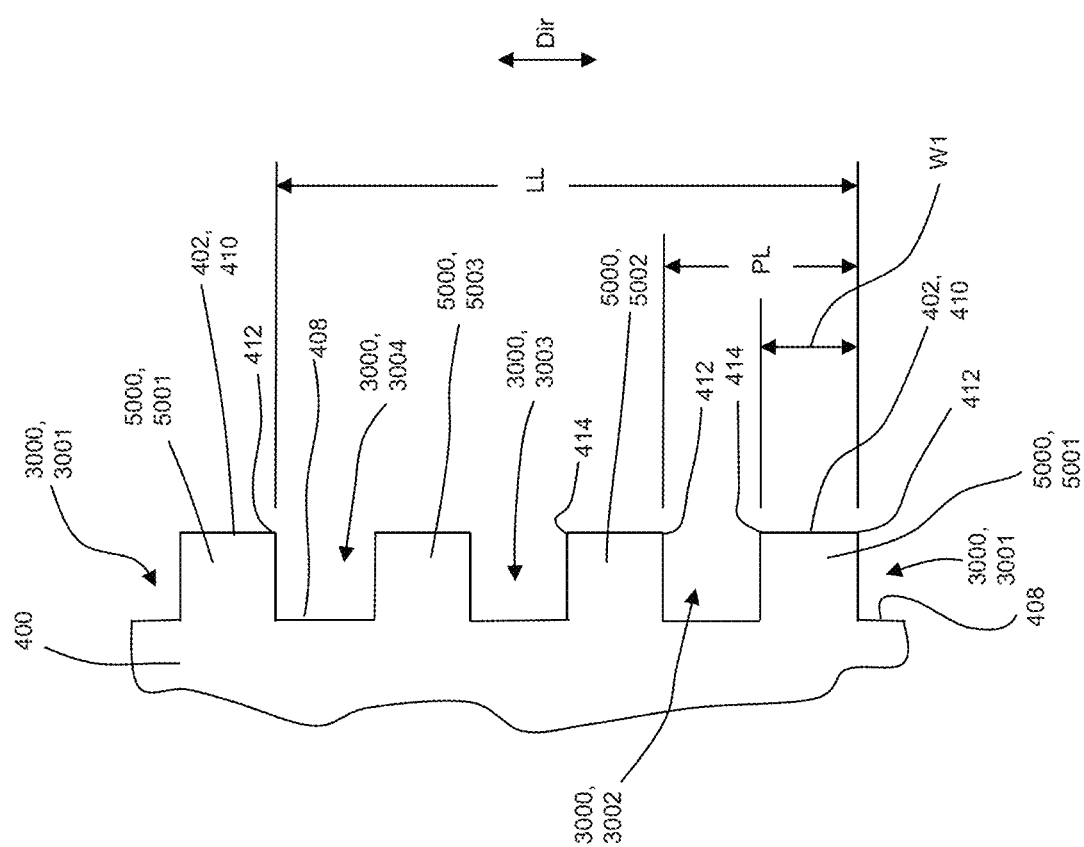
FIG. 13 is a detailed view of threads of the roll shown in FIG. 12.

As an example illustration, FIG. 12 shows the outer circumferential surface of the roll 400 shown in FIG. 11B laid out flat and modified to include three independent threads 5001, 5002, 5003 separated by four grooves 3001, 3002, 3003, 3004. And FIG. 13 is a detailed view of threads 5000 of the roll 400 shown in FIG. 12. As shown in FIGS. 12 and 13, the grooves 3000 may protrude radially inward into the roll 400 to define a second outer circumferential surface 408 of the roll 400. In turn, each thread 5000 may protrude radially outward from the second outer circumferential surface 408 to the first outer circumferential surface 402 of the roll 400. As such, each thread 5000 may include an outer circumferential surface 410 defined by a portion of the first outer circumferential surface 402 of the roll 400, wherein the outer circumferential surface 410 of each thread 5000 is positioned radially outward from the axis of rotation 404 by the first radius R1.

In the example shown in FIGS. 12 and 13, the outer circumferential surface 410 of each thread 5000 extends axially in the direction, Dir, from a first edge 412 to a second edge 414; to define a width, W1. It is to be appreciated that the threads 5000 may have various widths. For example, in some configurations, the width W1 defined by the distance between the first edge 412 and the second edge 414 may be at least about 1 mm. With continued reference to FIG. 13, the first edges 412 of neighboring threads 5000, such as first thread 5001 and second thread 5002, are separated by a pitch length, PL, extending in the direction Dir. As previously mentioned, and as shown in FIG. 12, the threads 5000 extend circumferentially around the axis of rotation 404 along helical paths parallel with each other. Because the number of threads, n, is 2 or greater, the first edges 412 of the first thread 5001 at various angular positions on the roll 400, from and between 0° and 360°, are separated from first edges of the first thread 5001 by a lead length, LL, extending in the direction Dir, wherein [LL=PL*n]. In addition, the first outer circumferential surface 402, which is positioned a distance R1 from the axis of rotation 404 of the roll, extends for a length CirL, wherein [CirL=2*ΠR1]. As such, each thread 5000 comprises a helix angle, HA, with respect to the direction Dir wherein:

[helix angle=arctan((2*Π*R1)/(LL)), wherein 45°<helix angle<90°].

It is to be appreciated that the rolls 400 herein may be configured with threads 5000 oriented at various helix angles. For example, in some configurations, the threads 5000 are oriented with helix angles greater than 45 degrees and less than 90 degrees, specifically reciting all 0.1 degree increments within the specified ranges and all ranges formed therein or thereby. It is also to be appreciated that the various numbers of threads may be created on the roll having various pitch lengths, PL, and various lead lengths, LL. For example, in some configurations, the pitch length, PL, is at least about 1.5 mm. In another example, the lead length, LL, is at least about 20 mm.

Figure 14:
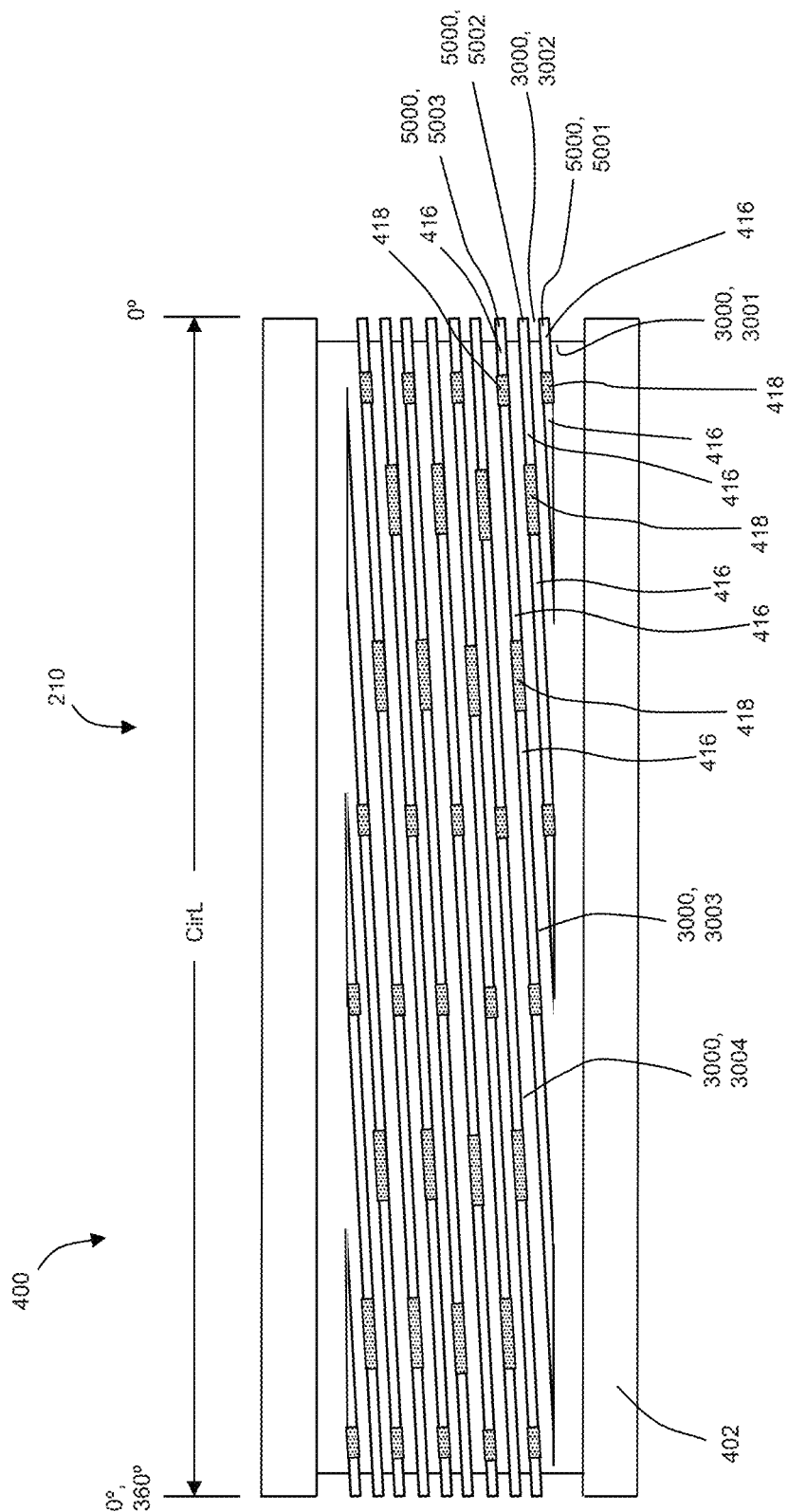
FIG. 14 is a view of an outer circumferential surface of the roll from FIG. 12 in the form of a pattern roll with portions of the threads modified to define pattern surfaces.
Figure 15A:
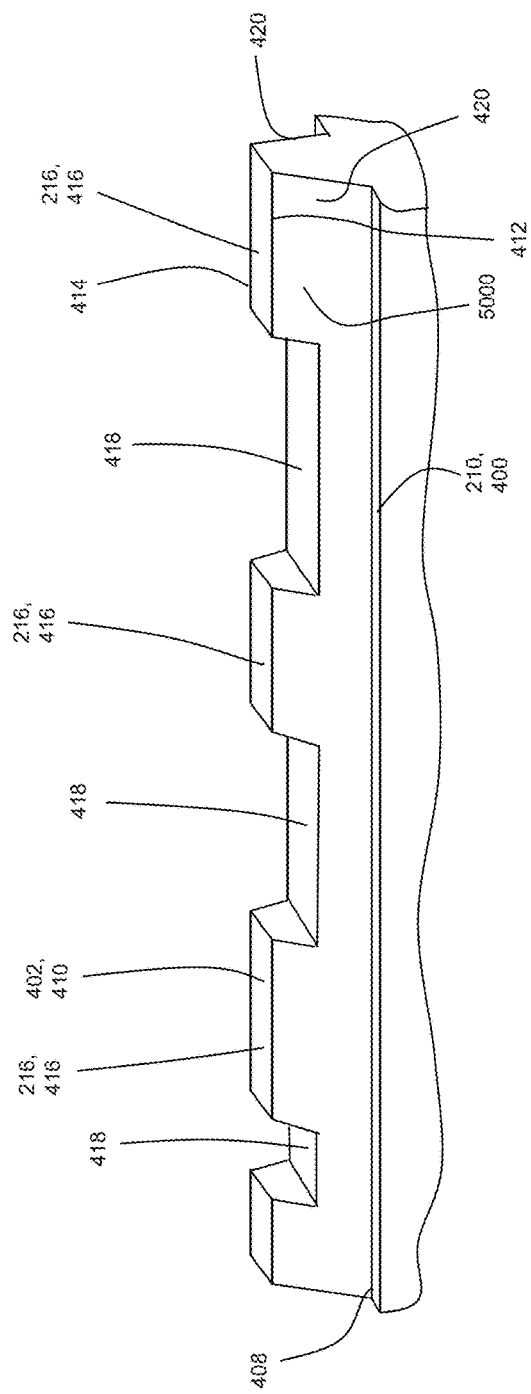
FIG. 15A is a detailed isometric view of a portion of a thread of a pattern roll with a tapered sidewall.
Figure 16A:
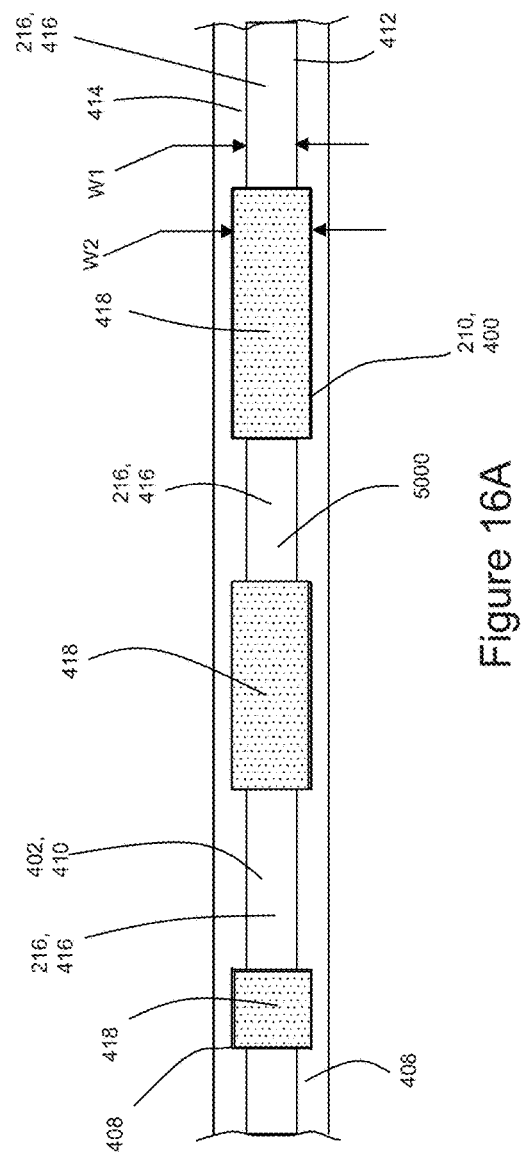
FIG. 16A is a top side view of the thread of the FIG. 15A.

Once the roll 400 is modified to include a desired number of threads 5000, the roll 400 may be converted into a pattern roll 210 by further modifying the threads 5000 to define pattern surfaces 216. For example, as shown in FIG. 14, the roll 400 of FIG. 12 may be further modified to form a pattern roll 210 by removing material from the outer circumferential surface 410 of each thread to form discrete first outer surfaces 416 and discrete second outer surfaces 418 on the threads 5000. It is to be appreciated that various processes may be used to remove material from the outer circumferential surface 410 of the threads, such as for example, hard milling. In FIGS. 14 and 16, the discrete second outer surfaces 418 are represented by shaded rectangles on the threads 5000. As shown in FIGS. 14-16, the discrete first outer surfaces 416 and discrete second outer surfaces 418 are intermittently arranged circumferentially around the axis of rotation 404 along a length of each thread 5000. As shown in FIG. 15, the discrete first outer surfaces 416 may be positioned radially outward from the axis of rotation by the first radius R1, and the discrete second outer surfaces 418 may be positioned radially outward from the axis of rotation 404 by a second radius R2 that less than the first radius R1. As such, the discrete first outer surfaces 416 define the pattern surfaces 216 of the pattern roll 210 discussed above. It is to be appreciated that R1 may have various values depending on particular design implementations or configurations. For example, in some configurations, R1 is at least about 100 mm. It is also to be appreciated that the discrete first outer surfaces 416 may be positioned at various distances radially outward from the discrete second outer surfaces 418. For example, in some configurations, R1 may be at least about 0.3 mm greater than R2. The discrete first outer surfaces 416 and the discrete second outer surfaces 418 may be positioned at various distances radially outward from the second outer circumferential surface 408 of the roll 400. For example, in some configurations, the discrete first outer surfaces 416 of the threads 5000 are positioned about 0.7 mm radially outward from the second outer circumferential surface 408 of the roll 400. In some configurations, the discrete second outer surfaces 418 of the threads 5000 are positioned about 0.4 mm radially outward from the second outer circumferential surface 408 of the roll 400. It is also to be appreciated that the threads 5000 may be configured in various shapes. For example, the thread 5000 shown in FIGS. 15A and 16A include tapered sidewalls 220. As such, the discrete first outer surface 416 or pattern surface 216 may define a width W1 and the discrete second outer surface 418 may define a width W2, wherein W2 is less than W1.

It is to be appreciated that the pattern rolls 210 herein may be configured in various ways with various patterns. For example, a single pattern roll may include a plurality of patterns in various zones, such as for example, a first zone having a first pattern, and a second zone having a second pattern. It is also to be appreciated that the pattern surfaces 216 may have various sizes and shapes. In some examples, pattern surfaces 216 may have a cross-directional width in the range of about 0.1 mm to about 10 mm, about 0.1 mm to about 5 mm, about 0.1 mm to about 3 mm, about 0.15 mm to about 2 mm, about 0.15 mm to about 1.5 mm, about 0.1 mm to about 1 mm, about 0.1 mm to about 0.5 mm, or about 0.2 mm to about 0.5 mm, specifically reciting all 0.05 mm increments within the specified ranges and all ranges formed therein or thereby. In some examples, the pattern surfaces 216 may have an aspect ratio that is greater than about 10:1.

In some examples, the pattern surfaces 216 may have an aspect ratio in the range of about 10:1, about 9:1, about 8:1, about 7:1, about 6:1, about 5:1, about 4:1, about 3:1, about 2:1, about 1.5:1, or about 1.1:1. It is to be appreciated that other aspect ratios of the pattern surfaces 216 are also within the scope of the present disclosure. In some examples, the spacing between adjacent pattern surfaces 216 in any direction may be greater than about 0.5 mm, greater than about 0.6 mm, greater than about 0.7 mm, greater than about 0.8 mm, greater than about 0.9 mm, greater than about 1 mm, greater than about 1.1 mm, greater than about 1.2 mm, greater than about 1.3 mm, greater than about 1.4 mm, greater than about 1.5 mm, greater than about 2 mm, greater than about 3 mm, or may be in the range of about 0.7 mm to about 20 mm, or about 0.8 mm to about 15 mm, specifically reciting all 0.1 mm increments within the specified ranges and all ranges formed therein or thereby.

As discussed above, it is to be appreciated that the pattern rolls 210 herein may be configured with various numbers of grooves 3000 and threads 5000 having various configurations of pattern surfaces 216. Thus, the pattern rolls 210 disclosed herein may be configured to create various types of patterns of discrete bond regions 306. In turn, such bond regions 306 may correlate generally with the patterns of apertures 308 created in the weakened precursor material 304 when utilized in the process discussed above with reference to FIGS. 3-10. As shown in FIGS. 11E and 11F, the threads 5000 may be substantially parallel and/or linear, and thus, the resulting bond regions 306 may also be substantially parallel and/or linear. In some configurations, the bond regions 306 may be formed in a non-linear fashion, such as for example, in waves. Also the bond regions 306 may be substantially linear and divergent over a portion of a pattern and/or convergent over a portion of a pattern. It is also to be appreciated that the grooves 3000 in the helical pattern may be configured to be align with each other. In some configurations, the grooves in one bond area could be offset from the grooves in an adjacent bond area.

Figure 17:
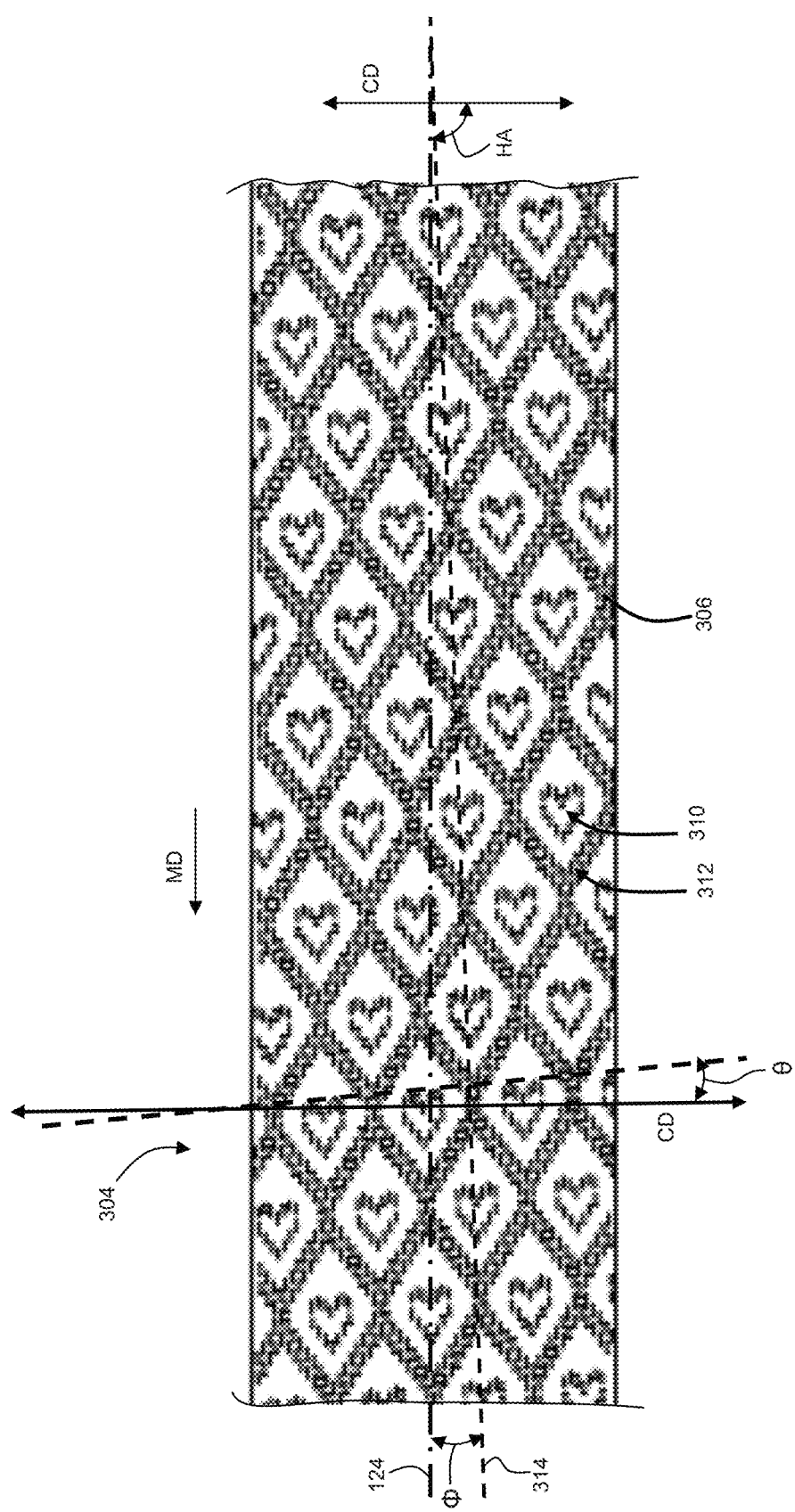
FIG. 17 is an example weakened precursor material including a pattern of discrete bond regions pattern made with a patterned roll.

FIG. 17 shows an example of a repeating patterns of discrete bond regions 306 imparted to a weakened precursor material substrate 304 by corresponding pattern surfaces 216 of a pattern roll 210. In the example shown in FIG. 17, the patterns are created with a pattern roll 216 having a plurality of independent threads 5000 arranged at a helix angle HA, such as discussed above. The threads 5000 include arrangements of pattern surfaces 216 that define a repeating pattern of heart shapes 310 and diamond shapes 312. As such, the pattern surfaces 216 and corresponding bond regions 306 are oriented at the helix angle HA with respect to the cross direction CD. As shown in FIG. 17, the pattern of heart shapes 310 and diamond shapes 312 progressively shift in the cross direction CD of the substrate 300 in accordance with the helix angle HA along the machine direction MD. The pattern surfaces 216 may also be arranged such that the patterns of heart shapes 310 and diamond shapes 312 may also be angularly offset with respect to the cross direction along the cross direction CD, as illustrated by angle, θ, in FIG. 17.

In an absorbent article context, the patterned apertured substrate 300 may be used as a topsheet or an outer cover nonwoven material. The absorbent article may have a central longitudinal axis 124 (see e.g., FIG. 1B) that extends in a direction generally parallel to the machine direction illustrated in FIG. 17. The patterns of heart shapes 310 and diamond shapes 312 may have a longitudinal axis 314 that extends at an angle, Φ, relative to the central longitudinal axis 124 of an absorbent article, wherein [Φ=90°−HA], and wherein the helix angle, HA, may be any of the angles disclosed herein. The absorbent articles may have any of the features and/or components described herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an apertured substrate, the method comprising:

rotating a pattern roll about an axis of rotation extending in a cross direction, the pattern roll comprising an outer circumferential surface, the pattern roll comprising: a number, n, of continuous threads extending circumferentially around the axis of rotation along a helical path parallel with each other, wherein n is 2 or greater; wherein each thread protrudes radially outward from the outer circumferential surface; wherein each thread comprises first outer surfaces and second outer surfaces intermittently arranged circumferentially around the axis of rotation along a length of each thread; wherein the first outer surfaces are positioned radially outward from the axis of rotation by a first radius R1; wherein the second outer surfaces are positioned radially outward from the axis of rotation by a second radius R2 less than the first radius R1; wherein each first outer surface extends axially in the cross direction, from a first edge to a second edge; wherein the first edges of neighboring threads are separated by a pitch length, PL, extending in the cross direction; wherein the first edges of a first thread are separated from first edges of the first thread by a lead length, LL, extending in the cross direction, wherein [LL=PL*n]; and wherein each thread comprises a helix angle, wherein

[helix angle=arctan((2*Π*R1)/(LL)), wherein 45°<helix angle<90°];

rotating an anvil roll adjacent the pattern roll;

advancing a substrate in a machine direction between the pattern roll and the anvil roll, the machine direction being substantially perpendicular to the cross direction;

compressing the substrate between the anvil roll and the first outer surfaces of the threads to form discrete bond regions in the substrate; and stretching the substrate in the cross direction to cause the discrete bond regions to rupture and form apertures.

2. The method of claim 1, wherein R1 is at least about 0.3 mm greater than R2.

3. The method of claim 1, wherein R1 is at least about 100 mm.

4. The method of claim 1, wherein the first surfaces of the threads are positioned about 0.7 mm radially outward from the outer circumferential surface.

5. The method of claim 1, wherein the pitch length, PL, is at least about 1.5 mm.

6. The method of claim 1, wherein the lead length, LL, is at least about 20 mm.

7. The method of claim 1, wherein number of threads, n, is greater than 2 and less than 25.

8. The method of claim 1, wherein a distance between the first edge and the second edge is at least about 1 mm.

9. The method of claim 1, wherein advancing a substrate further comprises combining a first substrate and a second substrate.

10. The method of claim 9, wherein the first and second substrates each comprise nonwovens.

11. An apparatus for bonding substrates comprising:
pattern roll adapted to rotate about an axis of rotation extending in a first direction D, the pattern roll comprising an outer circumferential surface, the pattern roll comprising:
a number, n, of continuous threads extending circumferentially around the axis of rotation along a helical path parallel with each other, wherein n is 2 or greater;
wherein each thread protrudes radially outward from the outer circumferential surface;
wherein each thread comprises first outer surfaces and second outer surfaces intermittently arranged circumferentially around the axis of rotation along a length of each thread;
wherein the first outer surfaces are positioned radially outward from the axis of rotation by a first radius R1; wherein the second outer surfaces are positioned radially outward from the axis of rotation by a second radius R2 less than the first radius R1;
wherein each first outer surface extends axially in the first direction, D, from a first edge to a second edge;
wherein the first edges of neighboring threads are separated by a pitch length, PL, extending in the direction D;
wherein the first edges of a first thread are separated from first edges of the first thread by a lead length, LL, extending in the direction D, wherein [LL=PL*n]; and
wherein each thread comprises a helix angle, wherein

[helix angle=arctan((2*Π*R1)/(LL)), wherein 45°<helix angle<90°]; and an anvil roll adjacent the pattern roll to define a nip between the first surfaces of the threads and the anvil roll.

12. The apparatus of claim 11, wherein R1 is at least about 0.3 mm greater than R2.

13. The apparatus of claim 11, wherein R1 is at least about 100 mm.

14. The apparatus of claim 11, wherein the first surfaces of the threads are positioned about 0.7 mm radially outward from the outer circumferential surface.

15. The apparatus of claim 11, wherein the pitch length, PL, is at least about 1.5 mm.

16. The apparatus of claim 11, wherein the lead length is at least about 20 mm.

17. The apparatus of claim 11, wherein number of threads, n, is greater than 2 and less than 25.

18. A method for making an apparatus for bonding substrates, the method comprising:
providing a roll adapted to rotate about an axis of rotation extending in a first direction D;
creating a plurality of grooves into the roll to form a number, n, of continuous threads extending circumferentially around the axis of rotation along a helical path parallel with each other, wherein n is 2 or greater, each thread comprising an outer circumferential surface extending axially in the first direction, D, from a first edge to a second edge; wherein the first edges of neighboring threads are separated by a pitch length, PL, extending in the direction D; wherein the first edges of a first thread are separated from first edges of the first thread by a lead length, LL, extending in the direction D, wherein [LL=PL*n]; and each thread comprising a helix angle, wherein

[helix angle=arctan((2*Π*R1)/(LL)), wherein 45°<helix angle<90];

removing material from the outer circumferential surface of each thread to form discrete first outer surfaces and discrete second outer surfaces intermittently arranged circumferentially around the axis of rotation along a length of each thread; wherein the first outer surfaces are positioned radially outward from the axis of rotation by a first radius R1; wherein the second outer surfaces are positioned radially outward from the axis of rotation by a second radius R2 less than the first radius R1; and positioning an anvil adjacent the roll to define a nip between the first outer surfaces and the anvil.

19. The method of 18, wherein creating a plurality of grooves further comprises grinding material from the roll.

20. The method of claim 18, wherein providing a roll further comprises: heat shrinking a sleeve onto an outer surface of a shaft.

* * * * *